US007176293B1

(12) United States Patent
Halazonetis et al.

(10) Patent No.: US 7,176,293 B1
(45) Date of Patent: Feb. 13, 2007

(54) COMPOSITIONS AND METHODS TO ENHANCE SENSITIVITY OF CANCER CELLS TO MITOTIC STRESS

(75) Inventors: Thanos Halazonetis, Wynnewood, PA (US); Daniel Scolnick, Merion, PA (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 343 days.

(21) Appl. No.: 10/048,046

(22) PCT Filed: Jun. 14, 2000

(86) PCT No.: PCT/US00/16391

§ 371 (c)(1),
(2), (4) Date: Jan. 24, 2002

(87) PCT Pub. No.: WO01/09150

PCT Pub. Date: Feb. 8, 2001

Related U.S. Application Data

(60) Provisional application No. 60/146,194, filed on Jul. 29, 1999.

(51) Int. Cl.
*C07H 21/02* (2006.01)
(52) U.S. Cl. .............. 536/23.1; 536/23.5; 536/24.33; 536/24.5; 435/91.1; 435/91.2; 435/94
(58) Field of Classification Search ............. 536/23.1, 536/23.5, 24.35, 24.5; 435/6, 91.1, 91.2, 435/94; 514/44
See application file for complete search history.

(56) References Cited

U.S. PATENT DOCUMENTS 5,324,630 A * 6/1994 LeFebvre et al. ............. 435/6
5,840,708 A * 11/1998 Weiss ........................ 514/44

FOREIGN PATENT DOCUMENTS

| EP | 1074617 A2 | 2/2001 |
| WO | WO99/11795 A1 | 3/1999 |
| WO | WO00/21991 A1 * | 4/2000 |

OTHER PUBLICATIONS

Bowie et al (Science, 1990, 257 : 1306-1310).*
Burgess et al, (Journal of Cell Biology, 1990, 11: 2129-2138).*
Lazar et al. Molecular and Cell Biology, 1988, 8: 1247-1252.*
Tao. et al. The Journal of Immunology, 1989, 143(8): 2595-2601.*
Gillies et al. Human Antibodies and Hybridomas , 1990, 1(1): 47-54.*
Tockman et al (Cancer Res., 1992, 52:2711s-2718s).*
Branch, AD, 1998, TIBS 23: 45-50.*
Gura (Science, 1995, 270:575-577).*
Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, p. 404-410).*
MPSRCH search report, 2004, us-10-048-046-1.oligo.rng, pp. 18-19.*
Boehringer Mannheim Biochemicals, 1994 Catalog, p. 93.*
Sambrook et al, 1989, Molecular cloning, a Laboratory manual, 2nd ed, Cold spring Harbor Laboratory Press, Cold Spring Harbor, p. 10.6-10.7.*
Sambrook et al, 1989, 2nd ed, Molecular cloning, A laboratory manual, Cold Spring Harbor laboratory Press, Cold Hpring Harbor, p. 10.13.*
JP06303997-A, 1994, GenBank Accession No:AAQ75652 and MPSRCH search report, 2005, us-10-048-046-1.oligo.rng, p. 2.*
US 5,610054-A, GenBank Accession No. I57653, and MPSRCH search report, 2005, us-10-048-046-1.copy 81-399.oligo.rge, p. 6.*
Gold, DP et al, 1993, GenBank Accession No. S86452 and MPSRCH search report, 2005, us-10-048-046-1.copy 997-1128. oligo.rge, pp. 3-4.*
George JF et al, 1992, GenBank Accession No. S81367, and MPSRCH search report, 2005, us-10-048-046-1.copy 1516-2013. oligo.rge, pp. 1, 4-5.*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764.*
G. Zhu et al, "The Fork Head Transcription Factor Hcm1p Participates in the Regulation of SPC110, Which Encodes the Calmodulin-Binding Protein in the Yeast Spindle Pole Body", Biochimica et Biophysica Acta, 1448(2):236-244 (Dec. 1998).
B. Ouyang et al, "Human Bub1: a Putative Spindle Checkpoint Kinase Closely Linked to Cell Proliferation", Cell Growth & Differentiation, 9(10):877-885 (Oct. 1998).
K. Hardwick, "The Spindle Checkpoint", Trends in Genetics, 14(1) 1-4 (Jan. 1998).
D. Cahill et al, "Mutations of Mitotic Checkpoint Genes in Human Cancers", Nature, 392:300-303 (Mar. 1998).
D. Scolnick et al, "Chfr Defines a Mitotic Stress Checkpoint that Delays Entry into Metaphase", Nature, 406(6794):430-435 (Jul. 2000).
D. Scolnick et al, "CHFR Prevents Chromosomal Condensation in Response to a Defective Spindle", Proceedings of the American Association for Cancer Research, 40:215, Abstract No. 1422 (Mar. 1999).

(Continued)

*Primary Examiner*—Jeffrey Siew
*Assistant Examiner*—Minh-Tam Davis
(74) *Attorney, Agent, or Firm*—Howson and Howson

(57) ABSTRACT

An isolated nucleic acid sequence of a mitotic checkpoint gene, chfr, encodes a Chfr protein having a Forkhead-associated domain and a Ring Finger. This protein is required for regulation of the transition of cells from prophase to metaphase during mitosis. The chfr nucleic acid and Chfr polypeptide are useful in diagnosing tumorigenic cells and in screening for drugs which can inhibit the activity of Chfr in a cancer cell, thereby rendering the cell more sensitive to additional anti-tumor therapies.

23 Claims, 12 Drawing Sheets

OTHER PUBLICATIONS

M. Murone et al, "The Fission yeast dma1 Gene is a Component of the Spindle Assembly Checkpoint, Required to Prevent Septum Formation and Premature Exit from Mitosis if Spindle Function is Compromised", EMBO J., 15(23):6605-6616 (Dec. 1996).

T. Isogai et al, "NEDO Human cDNA Sequencing Project", Database GenBank, Accession No. AK001658, (Feb. 16, 2000).

S. Elledge et al, "Mitotic Arrest: Mad2 Prevents Sleepy from Waking up the APC", Science, 279:99-100 (Feb. 1998).

A. Amon, "The Spindle Checkpoint", Current Opinion in Genetics & Development, 9:69-75 (1999).

L. Muhua et al, "A Cyotkinesis Checkpoint Requiring the Yeast Homologue of an APC-Binding Protein", Nature, 393:487-491 (Jun. 1998).

J. McIntosh et al, "Mitosis", Science, 246:622-628 (Nov. 1989).

M. Jordan et al, "Microtubules and Actin Filaments: Dynamic Targets for Cancer Chemotherapy", Current Opinion in Cell Biology, 10:123-130 (1998).

L. Hartwell et al, "Cell Cycle Control and Cancer", Science, 266 1821 1828 (Dec. 1994).

C. Lengauer et al, Genetic Instability in Colorectal Cancers, Nature, 386:623-627 (Apr. 1997).

C. Lengauer et al, "Genetic Instabilities in Human Cancers", Nature, 396:643-649 (Dec. 1998).

Y. Li et al, "Identification of a Human Mitotic Checkpoint Gene: hsMAD2", Science, 274:246-248 (Oct. 1996).

K. Yamaguchi et al, "Mutation Analysis of hBUB1 in Aneuploid HNSCC and Lung Cancer Cell Lines", Cancer Letters, 139:183-187 (1999).

D-Y. Jin et al., "Human T Cell Leukemia Virus Type 1 Oncoprotein Tax Targets the Human Mitotic Checkpoint Protein MAD1", Cell, 93:81-91 (Apr. 1998).

H. Zou et al, "Identification of a Vertebrate Sister-Chromatid Separation Inhibitor Involved in Transformation and Tumorigenesis", Science, 285:418-422 (Jul. 1999).

D. Cahill et al, "Characterization of MAD2B and Other Mitotic Spindle Checkpoint Genes", Genomics, 58:181-187 (1999).

Halazonetis, T.D., "Constitutively active DNA damage checkpoint pathways as the driving force for the high frequency of p53 mutations in human cancer", *DNA Repair (Amst).* Aug.-Sep. 2004 3(8-9):1057-1062.

Huyen et al., "Structural differences in the DNA binding domains of human p53 and its *C. elegans* ortholog Cep-1", *Structure (Camb).* Jul. 2004 12(7):1237-1243.

Mariatos et al., "Inactivating mutations targeting the *chfr* mitotic checkpoint gene in human lung cancer", *Cancer Res.* Nov. 1, 2003 63(21): 7185-7189.

Mochan et al., "53BP1, an activator of ATM in resopnse to DNA damage", *DNA Repair (Amst).* Aug.-Sep. 2004 3(8-9):945-952.

Mochan et al., "53BP1 and NFBDI/MDC1-Nbs1 function in parallel interacting pathways activating ataxia-telangiectasia mutated (ATM) in response to DNA damage", *Cancer Res.* Dec. 15, 2003 63(24): 8586-8591.

Stavridi et al., "p53 and stress in the ER", *Genes Dev.* Feb. 1, 2004 18(3):241-244.

Venere et al., "Chk2 leaves the PML depot", *Nature Cell Biol.* Nov. 2002 4(11):E255-E256.

Cortez et al., "Cell cycle: Conducting the mitotic symphony"*Nature* Jul. 27, 2000 406(6794):430-435.

NCBI Database Accession No. AA223491 "cDNA clone IMAGE:650972", 1996.

NCBI Database Accession No. AA223601 "cDNA clone IMAGE:650972", 1996.

NCBI Database Accession No. AA569875 "cDNA clone IMAGE:1071323", 1997.

\* cited by examiner

FIG. 1B

```
Rad53_sc    55   VLKEKRSIKKVWTFGRNPACDYHLG..........N I SRLSNKHFQ ILLGE.DGNLLLND.
                 | |                | |        |  |||||||||| |||||  |||||||
Chfr_hs     31   VLLRKRE.....WTIGRRRGCDLSFP..........S N KLVSGDHCRIVDEKSGQVTLED.
                 | ||               |||                | ||        |      |||
Dma1_sp     50   YWNRKQN.NLPIYIGRYTERYNGGDVS.......AIVFRSKVVSRRHAQIFYEN..NTWYIQDM
                 |||||||              |                || |||||||
YNL116w_sc  284  PI I RKAGPGSQLVIGRYTERVRDAISKIPEQYHPVVFKSKVVSRTHGCFKVDSQ.GNWYIKDV
                        :::                                      ::: :       :
                        IGR                                      ISR H  I         L D Rad53_sc    104  I STNGTWLNGQKVERN....SNQLLSQGDEI
                 |  |  |  |        |
Chfr_hs     77   TSTSGTVI NKL KVVKK....QTCPLQTGDVI
                 |||  |                | ||
Dma1_sp     104  GSSSGTFLNHV RLSP PSKTSKPY PI SNN DIL
                 ||||||||||| |||                  |||
YNL116w_sc  346  KSSSGTFLNHQ RLSPASSLSK DT PLRDGDIL
                   :::::::::  :                : :::
                   S N GTF N   R                L  GD I
```

FIG. 1C

```
ICP0_vzv    18   TCT ICMSTVSDLGKTM..PCDHDFCFV CI RAWTS...TSV QCPLCRCPV    61
                 ||  ||            ||||||| ||       ||| ||| |||||
Chfr_hs     303  TC I ICQDLLHDCVSLQ..PCMHTFCAACYSGWMERS...SLCPTCRCPV    346
                 ||  ||                ||   |  |         | || |||||
Dma1_ap     191  ECCICLMPVLP CQALFVAPCSHSYHYKCI RPTLN E SHPYFSCF ICRKYH   239
                 |   ||      ||  |  ||   |  ||           |   | | |
YNL116w_sc  432  DCSICLCK IKP CQAIF I SPCAHSWHFRCVRRL VMLSYPQFVCPNCRSSC  480
                 : ::        : ::     : ::  :       :              :: ::
                 C IC        C HFC   C      W                      CP  CR
``` wt *chfr*

5' ctcGTGgct
---------
3' gagCACcga

L  V  A

U2OS *chfr*

5' ctcATGgct
---------
3' gagTACcga

```
aagaattcgg cacgaggccg caatgtctct tgacagcggc ggcggcgcag ccggttccgg   60
gttcggcgcg gggcggggat gtgaatcccg atg gag cgg ccc gag gaa ggc aag  114
                                 Met Glu Arg Pro Glu Glu Gly Lys
                                  1                   5 cag tcg ccg ccg ccg cag ccc tgg gga cgg ctc ctg cgt ctg ggc gcg  162
Gln Ser Pro Pro Pro Gln Pro Trp Gly Arg Leu Leu Arg Leu Gly Ala
     10              15                  20 gag gag ggc gag ccg cac gtc ctc ctg agg aag cgg gag tgg acc atc  210
Glu Glu Gly Glu Pro His Val Leu Leu Arg Lys Arg Glu Trp Thr Ile
 25              30                  35                      40 ggg cgg aga cga ggt tgc gac ctt tcc ttc ccc agc aat aaa ctg gtc  258
Gly Arg Arg Arg Gly Cys Asp Leu Ser Phe Pro Ser Asn Lys Leu Val
             45                  50                  55 tct gga gat cac tgt aga att gta gtg gat gaa aaa tca ggt cag gtg  306
Ser Gly Asp His Cys Arg Ile Val Val Asp Glu Lys Ser Gly Gln Val
                 60                  65                  70 aca ctg gaa gat acc agc acc agt gga aca gtg att aac aag ctg aag  354
Thr Leu Glu Asp Thr Ser Thr Ser Gly Thr Val Ile Asn Lys Leu Lys
         75                  80                  85 gtt gtt aag aag cag aca tgc cct tta cag act ggg gat gtc atc tac  402
Val Val Lys Lys Gln Thr Cys Pro Leu Gln Thr Gly Asp Val Ile Tyr
 90                  95                 100 ttg gtg tac agg aag aat gaa ccg gaa cac aac gtg gca tac ctc tat  450
Leu Val Tyr Arg Lys Asn Glu Pro Glu His Asn Val Ala Tyr Leu Tyr
105             110                 115                     120 gaa tct tta agt gaa aag caa ggc atg aca caa gaa tcc ttt gaa gct  498
Glu Ser Leu Ser Glu Lys Gln Gly Met Thr Gln Glu Ser Phe Glu Ala
            125                 130                 135 aac aag gaa aat gtg ttc cat ggg acc aaa gat acc tca ggt gca ggt  546
Asn Lys Glu Asn Val Phe His Gly Thr Lys Asp Thr Ser Gly Ala Gly
        140                 145                 150 gca ggg cga ggg gcc gat ccc cgg gtc cct ccg tcg tcg ccc gcc act  594
Ala Gly Arg Gly Ala Asp Pro Arg Val Pro Pro Ser Ser Pro Ala Thr
        155                 160                 165 cag gtg tgc ttt gag gaa cca cag cca tca aca tcg acg tca gac ctc  642
Gln Val Cys Phe Glu Glu Pro Gln Pro Ser Thr Ser Thr Ser Asp Leu
    170                 175                 180 ttc ccc aca gcc tcg gcc tct tcc acg gag cct tct cct gca ggg cga  690
Phe Pro Thr Ala Ser Ala Ser Ser Thr Glu Pro Ser Pro Ala Gly Arg
185                 190                 195                 200 gag cgt tcc tcc agt tgt ggg tct ggg ggt ggt ggc atc tcc cct aaa  738
Glu Arg Ser Ser Ser Cys Gly Ser Gly Gly Gly Gly Ile Ser Pro Lys
                205                 210                 215
```

FIGURE 4B

```
gga agt ggt ccc tct gtg gca agt gat gaa gtc tcc agc ttt gcc tca    786
Gly Ser Gly Pro Ser Val Ala Ser Asp Glu Val Ser Ser Phe Ala Ser
            220                 225                 230 gct ctc cca gac aga aag act gcg tcc ttt tcg tcg ttg gaa ccc cag    834
Ala Leu Pro Asp Arg Lys Thr Ala Ser Phe Ser Ser Leu Glu Pro Gln
            235                 240                 245 gat cag gag gat ttg gag ccc gtg aag aag aaa atg aga gga gat ggg    882
Asp Gln Glu Asp Leu Glu Pro Val Lys Lys Lys Met Arg Gly Asp Gly
        250                 255                 260 gac ctt gac ctg aac ggg cag ttg ttg gtc gca caa ccg cgt aga aat    930
Asp Leu Asp Leu Asn Gly Gln Leu Leu Val Ala Gln Pro Arg Arg Asn
265                 270                 275                 280 gcc caa acc gtc cac gag gac gtc aga gca gcg gct ggg aag cca gac    978
Ala Gln Thr Val His Glu Asp Val Arg Ala Ala Ala Gly Lys Pro Asp
                285                 290                 295 aag atg gag gag acg ctg aca tgc atc atc tgc cag gac ctg ctg cac   1026
Lys Met Glu Glu Thr Leu Thr Cys Ile Ile Cys Gln Asp Leu Leu His
                300                 305                 310 gac tgc gtg agt ttg cag ccc tgc atg cac acg ttc tgc gcg gct tgc   1074
Asp Cys Val Ser Leu Gln Pro Cys Met His Thr Phe Cys Ala Ala Cys
            315                 320                 325 tac tcg ggc tgg atg gag cgc tcg tcc ctg tgt cct acc tgc cgc tgt   1122
Tyr Ser Gly Trp Met Glu Arg Ser Ser Leu Cys Pro Thr Cys Arg Cys
            330                 335                 340 ccc gtg gag cgg atc tgt aaa aac cac atc ctc aac aac ctc gtg gaa   1170
Pro Val Glu Arg Ile Cys Lys Asn His Ile Leu Asn Asn Leu Val Glu
345                 350                 355                 360 gca tac ctc atc cag cat cca gac aag agt cgc agt gaa gaa gat gtg   1218
Ala Tyr Leu Ile Gln His Pro Asp Lys Ser Arg Ser Glu Glu Asp Val
                365                 370                 375 caa agt atg gat gcc agg aat aaa atc act caa gac atg ctg cag ccc   1266
Gln Ser Met Asp Ala Arg Asn Lys Ile Thr Gln Asp Met Leu Gln Pro
            380                 385                 390 aaa gtc agg cgg tct ttt tct gat gaa gaa ggg agt tca gag gac ctg   1314
Lys Val Arg Arg Ser Phe Ser Asp Glu Glu Gly Ser Ser Glu Asp Leu
        395                 400                 405 ctg gag ctg tca gac gtt gac agt gag tcc tca gac att agc cag cca   1362
Leu Glu Leu Ser Asp Val Asp Ser Glu Ser Ser Asp Ile Ser Gln Pro
410                 415                 420 tac gtc gtg tgc cgg cag tgt cct gag tac aga agg cag gcg gcg cag   1410
Tyr Val Val Cys Arg Gln Cys Pro Glu Tyr Arg Arg Gln Ala Ala Gln
425                 430                 435                 440
```

FIGURE 4C

```
cct ccc cac tgc cca gca ccc gag ggc gag cca gga gcc cca cag gcc    1458
Pro Pro His Cys Pro Ala Pro Glu Gly Glu Pro Gly Ala Pro Gln Ala
            445             450             455 ctg ggg gat gca ccc tcc acg tcc gtc agc ctg acg aca gca gtc cag    1506
Leu Gly Asp Ala Pro Ser Thr Ser Val Ser Leu Thr Thr Ala Val Gln
            460             465             470 gat tac gtg tgc cct ctg caa gga agc cac gcc ctg tgc acc tgc tgc    1554
Asp Tyr Val Cys Pro Leu Gln Gly Ser His Ala Leu Cys Thr Cys Cys
            475             480             485 ttc cag ccc atg ccc gac cgg aga gcg gag cgc gag cag gac ccg cgt    1602
Phe Gln Pro Met Pro Asp Arg Arg Ala Glu Arg Glu Gln Asp Pro Arg
            490             495             500 gtc gcc cct cag cag tgt gcg gtc tgc ctg cag cct ttc tgc cac ctg    1650
Val Ala Pro Gln Gln Cys Ala Val Cys Leu Gln Pro Phe Cys His Leu
505             510             515             520 tac tgg ggc tgc acc cgg acc ggc tgc tac ggc tgc ctg gcc ccg ttt    1698
Tyr Trp Gly Cys Thr Arg Thr Gly Cys Tyr Gly Cys Leu Ala Pro Phe
            525             530             535 tgt gag ctc aac ctg ggt gac aag tgt ctg gac ggc gtg ctg aac aac    1746
Cys Glu Leu Asn Leu Gly Asp Lys Cys Leu Asp Gly Val Leu Asn Asn
            540             545             550 aac agc tac gag tca gac atc ctg aag aat tac ctg gca acc aga ggt    1794
Asn Ser Tyr Glu Ser Asp Ile Leu Lys Asn Tyr Leu Ala Thr Arg Gly
            555             560             565 ttg aca tgg aaa aac atg ttg acc gag agc ctc gtg gct ctc cag cgg    1842
Leu Thr Trp Lys Asn Met Leu Thr Glu Ser Leu Val Ala Leu Gln Arg
            570             575             580 gga gtg ttt ctg ctg tct gat tac aga gtc acg gga gac acc gtt ctg    1890
Gly Val Phe Leu Leu Ser Asp Tyr Arg Val Thr Gly Asp Thr Val Leu
585             590             595             600 tgt tac tgc tgt ggc ctg cgc agc ttc cgt gag ctg acc tat cag tat    1938
Cys Tyr Cys Cys Gly Leu Arg Ser Phe Arg Glu Leu Thr Tyr Gln Tyr
            605             610             615 cgg cag aac att cct gct tcc gag ttg cca gtg gcc gta aca tcc cgt    1986
Arg Gln Asn Ile Pro Ala Ser Glu Leu Pro Val Ala Val Thr Ser Arg
            620             625             630 cct gac tgc tac tgg ggc cgt aac tgc cgc act cag gtg aaa gct cac    2034
Pro Asp Cys Tyr Trp Gly Arg Asn Cys Arg Thr Gln Val Lys Ala His
            635             640             645 cac gcc atg aaa ttc aat cat atc tgt gaa cag aca agg ttc aaa aac    2082
His Ala Met Lys Phe Asn His Ile Cys Glu Gln Thr Arg Phe Lys Asn
650             655             660
```

FIGURE 4D

```
taagcatcca gaggccctga gcagctttca gcactggagg tgaagagagc gtgttttaa  2142
aatacagaga caagcacgtc aaggtgtttt cacagccccc tgagggaagg gacgcagggt  2202
ctccgacagg tgctctgggg tgactcttct gtggagcttt ttaccctctg agtgagaccc  2262
tccccagagc cccgggggcc gcagcccgcc ctcctggtga gcgctgggca gggctcgtgg  2322
tggcatcagc agcagagacg aagcctttct gtaacatgcg gccgtcccgc cgagagggc   2382
agttttgctc ttttgtacat tttccgaaac tacagttaaa gcagaagtct gttttcagga   2442
aaagtttcaa gggagaaggg caagtttatc aaaaacattg tttcaggaga agggagcata   2502
agtttacagc ctacaggacg tacacaatat cctgctgctg ggaaaaccac agcattttat   2562
ctattttta  ttttaatagg tttggtgctt atcttctaat aagatttaaa tgtcacaaac   2622
tgtagcacaa ataatataat ttataattta caaattgaca aaaaaaaaaa aaaaaa        2679
```

COMPOSITIONS AND METHODS TO ENHANCE SENSITIVITY OF CANCER CELLS TO MITOTIC STRESS

CROSS-REFERENCE TO RELATED APPLICATIONS

This is a 371 of PCT/US00/16391, filed Jun. 14, 2000, which claims the benefit of the priority of U.S. Patent Application No. 60/146,194, filed Jul. 29, 1999.

FIELD OF THE INVENTION

This invention relates generally to a novel gene, proteins encoded thereby, compositions containing same and methods of use therefor. More specifically, this invention relates to a novel cell cycle gene, and its uses in diagnosis and drug screening.

BACKGROUND OF THE INVENTION

Several critical processes occur during the four stages of mitotic cell division, which are prophase, metaphase, anaphase and telophase, including, without limitation, separation of the centrosomes and preparation of the cell to form the mitotic spindle; alignment of the chromosomes on the spindle in metaphase; and sister chromatid separation in anaphase. Specifically, during prophase the duplicated centrosomes migrate along the periphery of the nucleus towards opposite poles of the cell. During prophase the cell may also prepare for chromosome condensation and for other events that occur in metaphase. A critical and irreversible event during the transition from metaphase to anaphase is the irreversible segregation of sister chromatids between daughter cells.

The fidelity of mitosis is monitored by checkpoint genes. For example, a multitude of evolutionarily conserved checkpoint genes monitor the metaphase to anaphase transition. Several of these checkpoint genes have been identified, initially in yeast, and later in higher eukaryotes, that prevent the onset of anaphase until the mitotic spindle is properly assembled [Elledge, 1998, *Science*, 279:999–1000; Amon, 1999, *Curr. Opin. Genetics Dev.*, 9:69–75]. The presence of these checkpoint genes, coupled with the predisposition towards aneuploidy when these checkpoint genes are inactivated, provide evidence that this transition is clearly an important milestone for mitosis. Although most of the research on mitotic checkpoints has focused on the spindle checkpoint, which monitors the transition from metaphase to anaphase, given the complexity of the mitotic process, the existence of additional checkpoints that monitor other phases of mitosis is likely. A checkpoint monitoring the anaphase-to-telophase transition has been described [Muhua, L. et al, 1998 *Nature* 393: 487–491].

Errors during mitosis can result in unequal chromosome segregation and are probably responsible for the aneuploid phenotype of cancer cells. Agents that target microtubules induce mitotic stress and thus cause such errors [McIntosh, J. R. & Koonce, M. P., 1989 *Science*, 246:622–628; Jordan, M. A. & Wilson, L., 1998 *Curr. Opin. Cell Biol.*, 10: 123–130]. Many human cancers are sensitive to mitotic stress. This sensitivity is being exploited for therapy and implies that tumor cells have mitotic checkpoint defects [Lengauer et al., 1998, *Nature*, 396:643–649; Hartwell, L. H. & Kastan, M. B., 1994 *Science*, 266:1821–1828; Lengauer, C. et al, 1997 *Nature* 386:623–627; Lengauer, C. et al, 1998 *Nature* 396:643–649; Elledge, S. J. 1998 Science 279: 999–1000; Amon, A. 1999 *Curr. Opin. Genet. Dev.* 9: 69–75; and Li, Y. & Benezra, R., 1996 *Science*, 274: 246–248]. However, the known mitotic checkpoint genes, which prevent entry into anaphase when the chromosomes are not properly aligned on the mitotic spindle, are rarely inactivated in human cancer [Yamaguchi, K. et al, 1999 *Cancer Lett.* 139:183–187; Jin, D. Y. et al, 1998 *Cell* 93:81–91; Zou, H. et al, 1999 *Science* 285, 418–422]. For example, many of the mitotic spindle checkpoint genes have been examined for mutations in human cancer, but so far only infrequent bub 1 mutations have been detected [Cahill et al, 1998, *Nature*, 392:300–303; Cahill et al., 1999, *Genomics*, 58:181–187]. Thus, the molecular basis of cancer aneuploidy remains elusive, except for the small number of cases with bub 1 mutations.

Thus, there remains a need in the art for the identification of additional methods and compositions useful in the diagnosis of cancer, particularly the identification of additional genes that monitor and control mitosis, as well as methods and compositions that permit the screening of drugs useful for treatment of cancer. The present invention satisfies this need.

SUMMARY OF THE INVENTION

In one aspect, the invention provides an isolated nucleic acid sequence of a mitotic checkpoint gene, chfr, which encodes a Chfr protein having a Forkhead-associated (FHA) domain and a Ring Finger (RF) domain. The protein is required for regulation of the transition of cells from prophase to metaphase during mitosis.

In another aspect, the invention provides a substantially pure preparation of a polypeptide comprising an FHA domain and an RF domain. This protein is required for regulation of the transition of a normal human cell from prophase to metaphase during mitosis.

In still another aspect, the invention provides a method of determining tumorigenic potential of a cell comprising examining the cell for the presence of chfr nucleic acid sequence in the cell, wherein the absence of the chfr nucleic acid sequence indicates that the cell is sensitive to mitotic stress.

In yet another aspect, the invention provides a method of determining the tumorigenic potential of a cell comprising examining the cell for the presence of Chfr polypeptide expression in the cell, wherein the absence of the polypeptide sequence indicates that the cell is sensitive to mitotic stress.

In still another aspect, the invention provides a method for determining tumorigenic potential of a cell comprising examining the cell for mutations in the chfr gene, wherein the presence of mutations in the gene indicates that the cell is predisposed to tumorigenesis upon exposure to mitotic stress.

In another aspect, the invention provides a method for determining tumorigenic potential of a cell comprising examining the cell for Chfr-mediated ubiquitin-protein ligase activity, wherein the absence of this activity indicates that the cell is predisposed to tumorigenesis upon exposure to mitotic stress.

In a further aspect, the invention provides a diagnostic reagent comprising a nucleotide sequence that binds to the chfr nucleic acid sequence or a fragment thereof. The reagent sequence is preferably associated with a detectable label.

In still another aspect, the invention provides a diagnostic reagent comprising a ligand which binds to Chfr, the ligand associated with a detectable label.

Yet another aspect of this invention is a diagnostic kit for detecting the sensitivity of a cell to mitotic stress. The kit comprises at least one of the above-mentioned diagnostic reagents and suitable components for detection of the label.

In yet another aspect, the invention provides a ubiquitin-protein ligase assay useful for determining the activity and/or function of Chfr or screening for a Chfr inhibitor.

In still a further aspect, the invention provides a diagnostic kit for detecting the tumorigenic potential of a cell comprising components for a Chfr-mediated ubiquitin protein ligase assay.

In another aspect, the invention provides composition which inhibits the biological activity of Chfr. This inhibitor may be identified by one of the novel methods for identifying such inhibitors described herein.

Thus, in one aspect, a method of identifying a Chfr inhibitor is provided that comprises the steps of: (a) contacting a cell capable of expressing Chfr with a suitable amount of a test compound, and assessing the level of expression of Chfr in the cell; (b) assessing the level of expression of Chfr in an otherwise identical cell which has not been contacted with the test compound; and (c) comparing the levels of Chfr expression. A lower level of expression of the Chfr in the cell (a) compared with the level of Chfr in the cell (b) indicates that the test compound is a Chfr inhibitor.

In another aspect, the invention provides a method of identifying a Chfr inhibitor that comprises screening a test compound in a Chfr-mediated ubiquitin-protein ligase assay, wherein the substantial absence of, or reduction in, the ligase activity in the assay in the presence of the test compound indicates that the test compound inhibits Chfr function. This assay may involve contacting a mixture which normally demonstrates Chfr-mediated ubiquitin-protein ligase activity with a test compound; and assaying the mixture and test compound for the activity. The substantial absence of the activity in the presence of the test compound indicates that the test compound inhibits Chfr function.

In still a further aspect, the invention provides a method of retarding the growth of a cancer cell, the method comprising administering to the cell a Chfr inhibitor that enhances the sensitivity of the cell to mitotic stress. This method may be performed in vivo by direct administration to the mammal.

In still another aspect, a method of assessing the sensitivity of a tumor cell to an agent which disrupts microtubule function includes the steps of examining the cell for at least one of the following characteristics: the substantial absence of a chfr gene; the substantial absence of Chfr protein; the substantial absence of Chfr-mediated ubiquitin-protein ligase activity; and a mutation in the chfr gene. The identification of any of these characteristics provides an indication that the tumor cell is sensitive to an agent which disrupts microtubule function. The specific assay steps used in the determination are described herein.

Other aspects and advantages of the present invention are described further in the following detailed description of the preferred embodiments thereof.

BRIEF DESCRIPTION OF THE DRAWINGS

FIG. 1B illustrates the alignments of the FHA domains of *S. cerevisiae* Rad53 [SEQ ID NO:3], human chfr amino acids 31–103 of SEQ ID NO: 2, *S. pombe* Dma 1 [SEQ ID NO: 4], and the *S. cerevisiae* predicted open reading frame YNL116w [SEQ ID NO: 5]. The consensus (cons.) sequence of the FHA domains is also indicated.

FIG. 1C illustrates the alignments of the ring finger domains of the Varicella zoster virus ICP0 [SEQ ID NO: 6], human chfr amino acids 303 to 346 of SEQ ID NO: 2, *S. pombe* Dma 1 [SEQ ID NO:7], and *S. cerevisiae* predicted open reading frame YNL116w [SEQ ID NO:8]. The consensus (cons.) sequence of the RF domains is also indicated.

FIGS. 4A–4D illustrates the continuous chfr nucleotide sequence [SEQ ID NO:1], as well as the continuous amino acid sequence of Chfr [SEQ ID NO:2].

DETAILED DESCRIPTION OF THE INVENTION

Figure 1A:
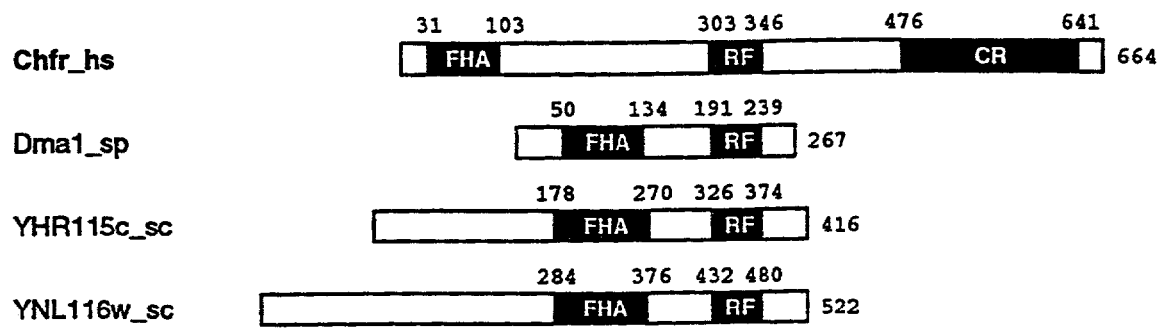
FIG. 1A is a schematic illustrating the structural domains of human Chfr (Chfr_hs), *S. pombe* Dma1 (Dma 1_sp), the *S. cerevisiae* predicted open reading frames YHR115c (YHR115c_sc) and YNL116w (YNL115c_sc). The FHA domain, the RF domain and the cysteine-rich (CR) region are indicated. The numbers refer to amino acid positions.

The invention relates to the discovery of a novel gene that functions as a mitotic checkpoint, and to the uses of the gene and the protein expressed therefrom in diagnostic, therapeutic and drug-screening applications.

A. The chfr Gene and Chfr Polypeptide

The novel mitotic checkpoint gene of this invention, referred to as chfr, is characterized by the presence of a ForkHead-Associated (FHA) DNA-binding domain and a ring finger motif FHA domains were initially identified in transcription factors that have forkhead DNA-binding domains and in protein kinases [Hofmann and Bucher, 1995, *Trends Bioch. Sci.*, 20:347–349]. Many proteins that contain FHA domains are currently recognized to be cell cycle checkpoints. Briefly described, the inventors identified this novel gene by screening a database of cDNA sequences for FHA domains. The human gene, hereafter referred to as chfr, has the nucleotide sequence reported in FIGS. 4A–4D [SEQ ID NO: 1]. The GenBank accession number for human Chfr is AF170724. This gene was noted to have weak similarity to the yeast mitotic checkpoint gene dma1. See, Example 1 below. The Chfr polypeptide expressed by this sequence has the amino acid sequence also reported in FIGS. 4A–4D [SEQ ID NO: 2]. Therefore, the invention includes an isolated chfr nucleic acid and also includes a substantially pure preparation of a Chfr polypeptide.

As disclosed in the Examples 2 and 3 below, Chfr expression is ubiquitous in normal tissues. However, in three of eight human cancer cell lines, chfr mRNA and Chfr protein were undetectable. In a fourth human cancer cell line, a missense mutation was identified. The Chfr polypeptide is thereby inactivated due to lack of expression or by mutation in four out of eight examined human cancer cell lines. Normal primary cells, e.g., diploid fibroblasts, and tumor cell lines that express wild-type chfr exhibited delayed entry into metaphase (i.e., arrested in prophase) when exposed to an agent which disrupts microtubule function and induces mitotic stress. These agents, such as nocodazole, the TAXOL™ drug and colcemid, inhibit centrosome separation. However, the tumor cell lines that have lost chfr function passed through prophase, entered metaphase without delay, and arrested in metaphase. Ectopic expression of wild-type chfr in these cells restored the cell cycle delay (e.g., prophase arrest) and increased the ability of the cells to survive mitotic stress. As discussed below, nocodazole inhibited centrosome separation, which normally occurs during prophase. Thus, cells that lack chfr function entered metaphase despite failure to separate the centrosomes. Such cells would be expected to have a high frequency of chromosome segregation errors and to survive mitotic stress less well than cells that retain chfr function. Thus, chfr defines a novel prophase to metaphase transition checkpoint that delays entry into metaphase in response to mitotic stress. A delay in metaphase entry in response to mitotic stress has not been previously described. When chfr is inactivated in human cancer cells, the inactivation contributes to aneuploidy and sensitivity to mitotic stress, e.g., such as that caused by agents that disrupt microtubule function or other chemotherapeutic agents.

Thus, in one embodiment, the invention includes an isolated nucleic acid of a chfr gene. The term "isolated nucleic acid" refers to a nucleic acid segment or fragment which has been separated from sequences which flank it in a naturally occurring state, e.g., a DNA fragment which has been removed from the sequences which are normally adjacent to the fragment, such as the sequences adjacent to the fragment in a genome in which it naturally occurs. The term also applies to nucleic acids which have been substantially purified from other components which naturally accompany the nucleic acid, e.g., RNA or DNA or proteins, in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic fragment produced by PCR or restriction enzyme digestion) independent of other sequences. It also includes a recombinant DNA which is part of a hybrid gene encoding additional polypeptide sequence.

The isolated nucleic acid of chfr according to this invention should not be construed as being limited solely to the nucleotide sequences presented herein, but rather should be construed to include any and all nucleotide sequences which share homology (i.e., have sequence identity) with the nucleotide sequences presented herein. Preferably, the invention includes an isolated nucleic acid having a nucleotide sequence which is at least 70% identical to the nucleotide sequence presented in FIG. 4A–4D. More preferably, an isolated nucleic acid of this invention has a nucleotide sequence which is at least 75% identical, even more preferably, 80% identical, yet more preferably, 85% identical, and even more preferably, 90% identical to the nucleotide sequence presented in FIGS. 4A–4D. Even more preferably, an isolated nucleic acid of this invention has a nucleotide sequence which is at least 95% identical, and most preferably, 99% identical, to the nucleotide sequence presented in FIGS. 4A–4D. Any such isolated nucleic acid would of course encode a polypeptide having the biological activity of the Chfr polypeptide disclosed herein.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGGC 5' share 50% homology. As used herein, "homology" is used synonymously with "identity".

Percent identity, percent similarity or percent homology of one polynucleotide or polypeptide with respect to another identified polynucleotide or polypeptide may be calculated using algorithms, such as the Smith-Waterman algorithm [J. F. Collins et al, 1988, *Comput. Appl. Biosci.*, 4:67–72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp. 417], and the BLAST and FASTA programs [E. G. Shpaer et al, 1996, *Genomics*, 38:179–191]. A preferred algorithm is the computer program BLAST, especially blastp or tblastn [Altschul et al, 1997 *Nucl. Acids Res.*, 25(17):3389–3402]. These references are incorporated herein by reference. Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. Unless otherwise specified, the parameters of each algorithm discussed above are the default parameters identified by the authors of such algorithms.

Among such homologous nucleotide sequences of this invention are allelic variants of the chfr sequences within a species (i.e., sequences containing some individual nucleotide differences from a more commonly occurring sequence within a species, but which nevertheless encode the same polypeptide or a protein with the same function). Additionally nucleic acid sequences capable of hybridizing under stringent conditions [see, J. Sambrook et al, *Molecular Cloning: A Laboratory Manual*, 2d ed., Cold Spring Harbor Laboratory (1989)] to the sequences of SEQ ID NO: 1, their anti-sense strands, or biologically active fragments thereof are homologous sequences according to this invention. An example of a highly stringent hybridization condition is hybridization in 2×SSC at 65° C., followed by a washing in 0.1×SSC at 65° C. for an hour. Alternatively, an exemplary highly stringent hybridization condition is in 50% formamide, 4×SSC at 42° C. Moderately high stringency conditions may also prove useful, e.g., hybridization in 4×SSC at 55° C., followed by washing in 0.1×SSC at 37° C. for an hour. An alternative exemplary moderately high stringency hybridization condition is in 50% formamide, 4×SSC at 30° C.

According to the invention, the chfr nucleic acid sequence may be modified. Utilizing the sequence data of SEQ ID NO: 1, it is within the skill of the art to obtain or prepare synthetically or recombinantly other polynucleotide sequences, or modified polynucleotide sequences, encoding the full-length Chfr protein or useful fragments of the invention. Such modifications at the nucleic acid level include, for example, modifications to the nucleotide sequences which are silent or which change the amino acids, e.g. to improve expression. Also included are allelic variations, caused by the natural degeneracy of the genetic code. Additional homologous sequences can include mutants including 5' or 3' terminal or internal deletions, which truncated or deletion mutant sequence may be expressed for the purpose of affecting the activity of the full-length or wild-type Chfr polypeptide or fragments.

In still another embodiment, the invention provides a substantially pure polypeptide of Chfr. The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The substantially pure preparation of Chfr according to this invention should not be construed as being limited solely to the amino acid sequences presented herein, but rather should be construed to include any and all amino acid sequences which share homology (i.e., have sequence identity) with the amino acid sequences presented herein. Preferably, the invention includes a polypeptide having an amino acid sequence which is 70% identical, more preferably, 75% identical, even more preferably, 80% identical, yet more preferably, 85% identical, even more preferably, 90% identical, more preferably, 95% identical and most preferably, 99% or 100% identical to the amino acid sequence presented FIGS. 4A–4D. This definition of the preparation of Chfr includes the definitions of "homologous", "homology" and "percent identity" as discussed above, including the list of computer algorithms available to calculate these homologies. Any such preparation of a homologous polypeptide has the biological activity of the Chfr polypeptide disclosed herein.

Also included in the invention are modified versions of the Chfr polypeptide. Typically, such polypeptides differ from the specifically identified Chfr polypeptide of FIGS. 4A–4D by only one to four codon changes. Examples include polypeptides with minor amino acid variations from the illustrated partial amino acid sequence of Chfr [SEQ ID NO: 2], in particular, conservative amino acid replacements. Conservative replacements are those that take place within a family of amino acids that are related in their side chains and chemical properties. Further encompassed by this invention are additional fragments of the Chfr polypeptide. These fragments may be designed or obtained in any desired length, including as small as about 5–8 amino acids in length. These small fragments may be useful as probes, primers, molecular weight markers, etc. However, all three fragments, the FHA domain (aa 31–103 of SEQ ID NO: 2), the RF domain (aa 303–346 of SEQ ID NO:2) and the cysteine-rich domain (aa 476 to 641 of SEQ ID NO:2), indicated as black boxes in FIG. 1A, are necessary for Chfr to have biological activity. Fragments of Chfr which are smaller than the full-length Chfr, but which possess these three domains, are desirably characterized by having a biological activity similar to that displayed by the complete Chfr polypeptide, including, e.g., the ability to delay entry into metaphase.

Chfr polypeptides of this invention may be characterized by measurements including, without limitation, western blot, macromolecular mass determinations by biophysical determinations, such as SDS-PAGE/staining, HPLC and the like, and assays such as those in the examples below to identify the biological activity. By the term "biological activity of Chfr" as used herein, is meant the ability to function as a checkpoint between prophase to metaphase in cells wherein in the absence or inactivation of the checkpoint sequence, the cells are predisposed to aneuploidy, and are sensitive to agents which disrupt microtubule function.

B. Methods of Preparing Sequences of this Invention

Methods for obtaining the nucleic acids and polypeptides of the invention should be apparent to those skilled in the art upon a reading of the present disclosure and by following any of the instructions in the art.

For example, the nucleotide and polypeptide sequences of the invention may be prepared conventionally by resort to known chemical synthesis techniques, e.g., solid-phase chemical synthesis, such as described by Merrifield, *J. Amer. Chem. Soc.*, 85:2149–2154 (1963), and J. Stuart and J. Young, *Solid Phase Peptide Synthelia*, Pierce Chemical Company, Rockford, Ill. (1984), or detailed in the examples below.

Alternatively, the nucleotide and polypeptide sequences of this invention may be prepared by known recombinant DNA techniques and genetic engineering techniques, such as polymerase chain reaction, by cloning and expressing within a host microorganism or cell a DNA fragment carrying a nucleic acid sequence encoding the above-described polypeptides, etc. [See, e.g., Sambrook et al., *Molecular Cloning. A Laboratory Manual.*, 2d Edit., Cold Spring Harbor Laboratory, New York (1989); Ausubel et al. (1997), Current Protocols in Molecular Biology, John Wiley & Sons, New York]. The Chfr may be obtained from gene banks derived from whole genomic DNA. These sequences, fragments thereof, modifications thereto and the full-length sequences may be constructed recombinantly using conventional molecular biology techniques, site-directed mutagenesis, genetic engineering or PCR, and the like by utilizing the information provided herein. For example, methods for producing the above-identified modifications of the sequences, include mutagenesis of certain nucleotides and/or insertion or deletion of nucleotides, or codons, thereby effecting the polypeptide sequence by insertion or deletion of, e.g., non-natural amino acids, are known and may be selected by one of skill in the art.

1. Expression In Vitro

To produce recombinant Chfr or other fragments of this invention in vitro (as well as to produce recombinant proteins of the ubiquitin-protein ligase assay described herein), the appropriate DNA sequences are inserted into a suitable expression system. Desirably, a recombinant molecule or vector is constructed in which the polynucleotide sequence encoding the selected protein is operably linked to a heterologous expression control sequence permitting expression of the protein. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known. See, Sambrook et al, *Molecular Cloning. A Laboratory Manual*, 2d edition, Cold Spring Harbor Laboratory, New York (1989); Miller et al, *Genetic Engineering*, 8:277–298 (Plenum Press 1986) and references cited therein.

Suitable host cells or cell lines for transfection by this method include bacterial cells. For example, the various strains of *E. coli* (e.g., HB101, MC1061, and strains used in the following examples) are well-known as host cells in the field of biotechnology. Various strains of *B. subtilis, Pseudomonas, Streptomyces*, and other bacilli and the like are also be employed in this method. Mammalian cells, such as human 293 cells, Chinese hamster ovary cells (CHO), the monkey COS-1 cell line or murine 3T3 cells derived from Swiss, Balb-c or NIH mice are used. Another suitable mammalian cell line is the CV-1 cell line. Still other suitable mammalian host cells, as well as methods for transfection, culture, amplification, screening, production, and purification are known in the art. [See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446]. Many strains of yeast cells known to those skilled in the art are also available as host cells for expression of the polypeptides of the present invention. Other fungal cells may also be employed as expression systems. Alternatively, insect cells such as *Spodoptera frugipedera* (Sf9) cells may be used.

Thus, the present invention provides a method for producing a recombinant Chfr protein, which involves transfecting, e.g., by conventional means such as electroporation, a host cell with at least one expression vector containing a polynucleotide of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art. For example, the proteins are isolated in soluble form following cell lysis, or extracted using known techniques, e.g., in guanidine chloride. If desired, the proteins or fragments of the invention are produced as a fusion protein to enhance expression of the protein in a selected host cell, to improve purification, or for use in monitoring the presence of the desired protein in tissues, cells or cell extracts. Suitable fusion partners for the proteins of the invention are well known to those of skill in the art and include, among others, β-galactosidase, glutathione-S-transferase, and poly-histidine.

2. Expression In Vivo

Alternatively, where it is desired that the Chfr protein of the invention or proteinaceous inhibitors thereof (whether full-length or a desirable fragment) be expressed in vivo, e.g., to induce antibodies, or as a therapeutic, an appropriate vector for delivery is readily selected by one of skill in the art. Exemplary vectors for in vivo gene delivery are readily available from a variety of academic and commercial sources, and include, e.g., adeno-associated virus [International patent application No. PCT/US91/03440], adenovirus vectors [M. Kay et al, *Proc. Natl. Acad. Sci. USA*, 91:2353 (1994); S. Ishibashi et al, *J. Clin. Invest.*, 92:883 (1993)], or other viral vectors, e.g., various poxviruses, vaccinia, etc. Methods for insertion of a desired gene, e.g., P7-1, and obtaining in vivo expression of the encoded protein, are well known to those of skill in the art.

The preparation or synthesis of the nucleotide and polypeptide sequences disclosed herein, whether in vitro or in vivo (including ex vivo) is well within the ability of the person having ordinary skill in the art using available material. The synthetic methods are not a limitation of this invention.

C. Inhibitors of chfr or Chfr of the Invention and Compositions Containing Them

In still another embodiment, the invention provide inhibitors of the chfr gene or Chfr polypeptide. Such inhibitor compositions have utility as diagnostic reagents or as therapeutic reagents in the methods described below. By the use of the term "chfr inhibitor" as used herein is meant a compound which is capable of inhibiting expression and or biological activity of Chfr. Inhibition of Chfr activity, function or expression may be assessed by following the procedures presented in the examples herein, which permit the progress (or the lack thereof) of a cell from prophase to metaphase to be monitored.

1. Nucleotide Sequence Inhibitors

One such inhibitor is a nucleotide sequence that binds to the chfr nucleic acid sequence or a fragment thereof. Such inhibitors when contacted with a cell expressing chfr inhibit the expression of (or inactivate) Chfr in that cell. For example, an inhibitor of chfr expression or function includes an oligonucleotide molecule which is preferably in an antisense orientation with respect to the nucleic acid sequence of chfr. As used herein, the term "antisense oligonucleotide" means a nucleic acid polymer, at least a portion of which is complementary to a chfr nucleic acid. "Antisense" refers particularly to the nucleic acid sequence of the noncoding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The antisense oligonucleotides of the invention preferably comprise between about fourteen and about fifty nucleotides. More preferably, the antisense oligonucleotides comprise between about twelve and about thirty nucleotides. Most preferably, the antisense oligonucleotides comprise between about sixteen and about twenty-one nucleotides. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art [U.S. Pat. No. 5,034,506; Nielsen et al., 1991, *Science* 254: 1497].

2. Polypeptide/Protein inhibitors

In another embodiment, another inhibitor composition of the invention includes a ligand which binds to Chfr polypeptide. Such a ligand is desirably an antibody which binds to Chfr, thereby inhibiting the function thereof. The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, high affinity polyclonal antibodies, monoclonal antibodies, synthetic antibodies, chimeric antibodies, recombinant antibodies and humanized antibodies. Such antibodies may originate from immunoglobulin classes IgG, IgM, IgA, IgD and IgE. Such antibodies may include a Fab, Fab' or F(ab')2, or Fc antibody fragment thereof which binds Chfr. Still another useful ligand is a single chain Fv antibody fragment which binds Chfr.

Another useful ligand is a recombinant construct comprising a complementarity determining region of an antibody, a synthetic antibody or a chimeric antibody construct or a humanized antibody construct which shares sufficient CDRs to retain functionally equivalent binding characteristics of an antibody that binds Chfr. By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The antibodies of this invention are generated by conventional means utilizing the isolated, recombinant or modified Chfr or fragments thereof as antigens of this invention. For example, polyclonal antibodies are generated by conventionally stimulating the immune system of a selected animal or human with a Chfr antigen, allowing the immune system to produce natural antibodies thereto, and collecting these antibodies from the animal or human's blood or other biological fluid. Preferably a recombinant version of Chfr is used as an immunogen. Monoclonal antibodies (MAbs) directed against Chfr are also generated conventionally. Hybridoma cell lines expressing desirable MAbs are generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., *Science*, 233:747–753 (1986); Queen et al., *Proc. Nat'l. Acad. Sci. USA*, 86:10029–10033 (1989); PCT Patent Application No. PCT/WO9007861; and Riechmann et al., *Nature*, 332:323–327 (1988); Huse et al, *Science*, 246:1275–1281 (1988)]. Given the disclosure contained herein, one of skill in the art may generate ligands or antibodies directed against Chfr by resort to known techniques by manipulating the complementarity determining regions of animals or human antibodies to the antigen of this invention. See, e.g., E. Mark and Padlin, "Humanization of Monoclonal Antibodies", Chapter 4, *The Handbook of Experimental Pharmacology*, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, *Proc. Natl. Acad. Sci. USA* 85:5879–5883; and Bird et al., 1988, *Science* 242:423–426.

Alternatively, Chfr antigens are assembled as multi-antigenic complexes [see, e.g., European Patent Application 0339695, published Nov. 2, 1989] and employed to elicit high titer antibodies capable of binding the Chfr. Further provided by the present invention are anti-idiotype antibodies (Ab2) and anti-anti-idiotype antibodies (Ab3). Ab2 are specific for the target to which anti-Chfr antibodies of the invention bind and Ab3 are similar to Chfr antibodies (Ab1) in their binding specificities and biological activities [see, e.g., M. Wettendorff et al., "Modulation of anti-tumor immunity by anti-idiotypic antibodies." In *Idiotypic Network and Diseases*, ed. by J. Cerny and J. Hiernaux J, Am. Soc. Microbiol., Washington D.C.: pp. 203–229, (1990)]. These anti-idiotype and anti-anti-idiotype antibodies are produced using techniques well known to those of skill in the art. Such anti-idiotype antibodies (Ab2) can bear the internal image of Chfr and are thus useful for the same purposes as Chfr.

In general, polyclonal antisera, monoclonal antibodies and other antibodies which bind to Chfr as the antigen (Ab1) are useful to identify epitopes of Chfr to separate Chfr and its analogs from contaminants in living tissue (e.g., in chromatographic columns and the like), and in general as research tools and as starting material essential for the development of other types of antibodies described above. Anti-idiotype antibodies (Ab2) are useful for binding the same target and thus may be used in place of Chfr to induce useful ligands to Chfr. The Ab3 antibodies are useful for the same reason the Ab1 are useful. Other uses as research tools and as components for separation of Chfr from other contaminants, for example, are also contemplated for the above-described antibodies.

Other ligands may include small chemical compounds that are screened in the ubiquitin-ligase assay described below and that are found to inhibit this enzymatic activity or other activities of Chfr. Such Chfr ligands or inhibitors may be identified and developed by the drug screening methods discussed in detail below.

3. Inhibitors as Diagnostic Reagents and Kits

For use in diagnostic assays and kits, the above-described inhibitors of the chfr gene and Chfr polypeptide are preferably associated with a detectable label which is capable, alone or in concert with other compositions or compounds, of providing a detectable signal. Where more than one reagent sequence or Chfr inhibitor is employed in a diagnostic method, the labels are desirably interactive to produce a detectable signal. Most desirably, the label is detectable visually, e.g. colorimetrically. A variety of enzyme systems operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that may be utilized in the methods of this invention are detectable by other means, e.g., colored latex microparticles [Bangs Laboratories, Indiana] in which a dye is embedded may be used in place of enzymes to form conjugates with the inhibitor sequences or ligands and provide a visual signal indicative of the presence of the resulting complex in applicable assays. Still other labels include fluorescent compounds, radioactive compounds or elements. Preferably, each reagent or ligand is associated with, or conjugated to a fluorescent detectable fluorochromes, e.g., fluorescein isothiocyanate (FITC), phycoerythrin (PE), allophycocyanin (APC), coriphosphine-O (CPO) or tandem dyes, PE-cyanin-5 (PC5), and PE-Texas Red (ECD). All of these fluorescent dyes are commercially available, and their uses known to the art.

Detectable labels for attachment to reagent sequences and antibodies useful in diagnostic assays of this invention may be easily selected from among numerous compositions known and readily available to one skilled in the art of diagnostic assays. The diagnostic reagents and ligands of this invention are not limited by the particular detectable label or label system employed.

Methods for coupling or associating the label with the reagent sequence or ligand are similarly conventional and known to those of skill in the art. Known methods of label attachment are described [see, for example, Handbook of Fluorescent Probes and Research Chemicals, 6th Ed., R. P. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

For convenience, the conventional reagents for ELISA or other diagnostic assays according to this invention may be provided in the form of kits. Such kits are useful for determining the absence (e.g., inactivation) or presence of chfr gene or Chfr polypeptide in a cell, particularly a tumor cell. Thus, such a kit will be useful in conducting the diagnostic assays discussed below, e.g., in determining if a cell is tumorigenic, in determining the status of treatment of a cancer, etc. Such a diagnostic kit contains a nucleotide reagent sequence (e.g., a chfr antisense sequence), or Chfr inhibitor (e.g., an antibody capable of binding Chfr) of this invention. Alternatively, such kits may contain a simple mixture of such inhibitors or means for preparing a simple mixture. The kits also include instructions for performing the assay, microtiter plates to which the inhibitors or nucleic acid sequences of the invention have been pre-adsorbed, various diluents and buffers, labeled conjugates for the detection of specifically bound compositions and other signal-generating reagents, such as enzyme substrates, cofactors and chromogens. Other components may include indicator charts for colorimetric comparisons, disposable gloves, decontamination instructions, applicator sticks or containers, and a sample preparator cup. Such kits provide a convenient, efficient way for a clinical laboratory to diagnose the tumorigenic potential of a mammalian cell according to this invention.

Still another variant of a diagnostic kit for detecting the tumorigenic potential of a cell contains the components necessary for a Chfr-mediated ubiquitin protein ligase assay, such as the assay described below. Such components may include the human E1 ubiquitin activating enzyme and the human E2 ubiquitin-conjugating enzyme, ubiquitin, ATP, an anti-ubiquitin antibody, an immobilized agent capable of binding labeled Chfr, as well as reagents necessary for performing gel electrophoresis and immunoblotting. Similarly, the non-biologic materials necessary for performing such an assay (as described above) may be included in this kit.

One of skill in the art may be expected to vary the components of these diagnostic kits in obvious ways based on the knowledge in the art coupled with this disclosure. Such varied components are considered to be encompassed in this embodiment of the invention.

4. Inhibitors as Therapeutic Compositions of this Invention Alternatively, an above-described inhibitor of Chfr of this invention may be employed therapeutically, and as such, is encompassed in a pharmaceutical composition. Such a composition includes a Chfr inhibitor (nucleotide or polypeptide or protein, or a small chemical compound) and a pharmaceutically-acceptable carrier. As used herein, the term "pharmaceutically-acceptable carrier" means a chemical composition with which an appropriate Chfr inhibitor may be combined and which, following the combination, can be used to administer the appropriate Chfr inhibitor to a mammal. For example, suitable carriers include saline, buffered saline, and the like. In addition to the appropriate Chfr inhibitor, such pharmaceutical compositions may also contain other ingredients known to enhance and facilitate drug administration. Other possible formulations, such as nanoparticles, liposomes, resealed erythrocytes, and immunologically based systems may also be used to administer an appropriate Chfr inhibitor according to the methods of the invention.

Also, as noted herein, pharmaceutical compositions of this invention may include a combination of compounds comprising a Chfr inhibitor and another chemotherapeutic agent, particularly an agent which disrupts microtubule function. Among such agents that disrupt microtubule function include nocodazole, the TAXOL™ drug and colcemid. Other such agents known in the art, or that may be developed in the future should be useful in this context.

Pharmaceutical compositions that are useful in the methods of the invention may be administered systemically by conventional therapeutic routes, e.g., intravenously, intraperitoneally, orally, via the mucosa, intramuscularly, subcutaneously, transdermally, topically, etc. Formulations suitable for the selected route can include, among others, oral solid formulations, ophthalmic, suppository, aerosol, topical or other similar formulations that may be designed using information known to one of skill in the pharmaceutical formulations art. Selection of the formulations and routes are within the skill of the art, and are not a limitation of this invention.

D. Methods Using the Compositions of this Invention

According to the present discovery, chfr is required for regulation of the transition of cells from prophase to metaphase. Thus, the absence of functional chfr in a cell, or the presence of insufficient Chfr in a cell has ramifications with respect to whether a cell will become a tumor cell. Methods of this invention involve the use of the chfr nucleotide sequences, Chfr polypeptide sequences as well as the Chfr inhibitors in diagnostic and therapeutic protocols.

1. Diagnostic Methods of the Invention

Because cells which lack proper checkpoints in the cell cycle are more likely to develop into tumor cells, the invention includes methods of identifying a cell which is likely to become a tumor cell using the above-described compositions. In one embodiment, a method of determining tumorigenic potential of a mammalian cell includes examining the cell for the presence of, or mutations in, the chfr nucleic acid sequence. The substantial absence of, or mutation in, a chfr nucleic acid sequence indicates that the cell is predisposed to tumorigenesis, particularly upon exposure to an agent or environment that is capable of inducing mitotic stress in the cell.

The detection of a chfr gene in a cell may be assessed in any ordinary nucleic acid expression assay, including techniques such as, Northern blotting with a suitable nucleic acid probe, Southern blotting, polymerase chain reaction (PCR), reverse transcriptase-PCR, RNase protection assays and in situ hybridization and the like. Such assays may readily be employed in vitro by exposing a sample of tissue to be examined for tumorigenic potential to an anti-sense oligonucleotide, PCR primer or other chfr inhibitor of this invention. See, for example, the protocol of Example 2 below. Such assay techniques are conventional and the protocols for these assays are found in standard texts, such as Sambrook et al, cited above.

Another embodiment of a nucleic acid assay for use in determining the tumorigenic potential of a cell includes the steps of examining the cell for mutations in the chfr gene. The presence of mutations in the gene indicates that the cell is predisposed to tumorigenesis upon exposure to mitotic stress. This method involves isolating nucleic acid from the cells of selected species of mammal (preferably human) or other animal. This can be accomplished using either RNA or genomic DNA and using fragments of the chfr gene of this invention as the primers. The sequences obtained from the cells using RT-PCR for RNA or PCR for DNA are then amplified and the resulting gene sequenced to uncover any mutations. In order to examine the sequence for mutations, any conventional technique may be used, such as in situ hybridization. By this means the sequence from the cell under examination is compared to the sequence of a normal chfr gene to determine if the chfr gene of the cell bears a mutation. Techniques for comparison include conformation sensitive gel electrophoresis or single strand polymorphism analysis, among others. [See, Sambrook et al, or other conventional texts]. If desired, the sequence may be used to express a polypeptide, and that polypeptide may be tested to determine if it retains a function of Chfr, such as Chfr-mediated ubiquitin-protein ligase activity, or other functions as disclosed herein. Any mutations in these sequences that inactivate the Chfr function may be employed in methods and compositions of this invention.

In another embodiment, the invention provides a method of determining tumorigenic potential of a cell comprising examining the cell for the presence of Chfr polypeptide expression. The absence of a detectable level of Chfr polypeptide indicates that the cell is predisposed to tumorigenesis upon exposure to mitotic stress. The method also comprises determining whether or not Chfr is expressed at a lower than normal level in a cell, wherein a lower level of expression of Chfr in the cell, compared with expression of Chfr in an otherwise identical normal cell, is an indication that the cell will develop into a tumor cell.

Cells may be examined for expression of Chfr polypeptide using conventional protein and immunological assays, such as, without limitation, western immunoblotting with a suitable antibody, ELISA, immunofluorescence and immunochemistry [see, e.g., Sambrook et al, and other texts for such assay steps]. Such assays may readily be employed in vitro by exposing a sample of tissue to be examined for tumorigenic potential to a Chfr inhibitor, e.g., an antibody of this invention as described above.

Still another embodiment of a method for determining the tumorigenic potential of a cell involves examining the cell for Chfr-mediated ubiquitin-protein ligase activity. As one embodiment, a diagnostic in vitro assay format involves capturing Chfr from cells on beads using antibodies that recognize Chfr. The beads may be conventional styrene or other beads which are conjugated to protein G or protein A, which have the capability of capture antibodies, such as the anti-Chfr antibody. The beads are then incubated with the E1 and E2 ubiquitin enzymes, ubiquitin and ATP. In the presence of these enzymes, any Chfr protein normally produced in the cell will be ubiquitinated (will associate with ubiquitin). The beads are washed to remove all protein except the Chfr which is captured on the beads by the protein A or protein G. Chfr is then eluted from the beads using, e.g., a sodium dodecyl-sulfate (SDS)-sample buffer. The released Chfr is then subjected to SDS gel electrophoresis and immunoblotting with an anti-ubiquitin antibody. If Chfr is ubiquitinated, than the anti-ubiquitin antibodies will recognize the Chfr protein indicating the cell has Chfr-mediated ubiquitin-protein ligase activity. If the cell has such activity, the cell contains functional Chfr. The absence (or substantial reduction) of such activity indicates that the cell does not have functional Chfr and is therefore predisposed to tumorigenesis upon exposure to mitotic stress. See, e.g., Example 5 below. In this assay, the Chfr antibody released from the protein A or protein G conjugated beads may also be ubiquitinated and may also serve as a ubiquitination substrate to monitor Chfr-mediated ubiquitin protein ligase activity in other formats of this assay.

As stated herein, cells which lack chfr function are more sensitive to agents which disrupt microtubule function than are cells which have chfr function. Thus, the invention further includes a method of determining the sensitivity of a tumor cell in a mammal to agents which disrupt microtubule function or to other chemotherapeutic agents. The methods described in detail above can be used to assess the cell for one or more of the characteristics including the substantial absence of a chfr gene; the substantial absence of Chfr protein; the substantial absence of Chfr-mediated ubiquitin-protein ligase activity; and/or a mutation in the chfr gene. The identification of any of these characteristics provides an indication that said tumor cell is sensitive to an agent which disrupts microtubule function. Thus, for example, the method can include assessing ex vivo the level of Chfr expression at the nucleic acid or protein level in the mammalian cell, which has been identified as a tumor cell. This experimental level is then compared to the level of Chfr expression in a non-tumor cell of the mammal. A lower level of expression of Chfr or the absence of Chfr expression or function in the cell compared with the level of expression of Chfr in an otherwise identical mammalian non-tumor cell, is an indication that the cell is sensitive to agents which disrupt microtubule function. This method can include assessing the cell for chfr gene mutations, as described above. Further, this method can include assessing the cell for Chfr-mediated ubiquitin-protein ligase activity, as described above.

Knowledge of the sensitivity of a tumor cell in a mammal to an agent which disrupts microtubule function may be used to determine the type of chemotherapeutic agent which might be administered to the mammal to kill the tumor cell. For example, the cells so identified may thereafter be exposed to a battery of such microtubule disrupting agents and/or other chemotherapeutic agents to enable the selection of the agent most effective in killing the tumor cells in an ex vivo or in vivo therapeutic context.

Similarly, as described above for nucleic acid assays, amplified RNA or DNA from the cells of a variety of mammalian (or other animal) species may be examined and/or expressed and assayed to detect mutations that inactivate the function of Chfr.

2. Therapeutic Methods of this Invention

As the data presented in the following examples establish, inactivation of Chfr function or a lower level of expression thereof in human cancer has two effects. First, it predisposes the cell to aneuploidy, as cells that condense their chromosomes without having separated their centrosomes have difficulty forming an intact mitotic spindle. Second, it increases the sensitivity of cancer cells to mitotic stress. Thus, cancer cells lacking Chfr function would be sensitive to agents, such as nocodazole and the TAXOL™ drug, that disrupt microtubule function, as demonstrated experimentally with the DLD1-neo and DLD1-chfr cells in the examples below Thus, the present invention also provides a therapeutic method of retarding the growth of, or killing, tumor cells, by inhibiting expression of Chfr in cells which are tumor cells. Since the development of tumor cells occurs via a vast number of mechanisms, the tumor cells to be killed need not necessarily have arisen due to a lack of adequate expression of Chfr. Indeed, the method of killing tumor cells is likely to be more effective in cells in which Chfr is expressed, and which have developed into tumor cells via a Chfr-independent mechanism. In this instance, inhibition of Chfr expression results in a tumor cell which is more sensitive to mitotic stress and is therefore more sensitive to agents, such as nocodazole and the TAXOL™ drug, that disrupt microtubule function.

Thus, in another embodiment a therapeutic method of the invention comprises administering to a mammalian tumor cell, preferably in vivo, an inhibitor of Chfr expression or biological activity, such as the reagent antisense sequences and/or the protein ligands, and/or small chemical compounds described above in a dosage which is suitable to retard or inhibit expression or function of Chfr in the cell. This inhibition results in enhanced sensitivity of the tumor cell to mitotic stress, and thereby enhances the sensitivity of the cell to an agent which disrupts microtubule function. Such a method is also useful for killing a tumor cell. Thus, an optional step in this therapeutic method is administering to the tumor cell, or to the mammal bearing the tumor cell an agent which disrupts microtubule function in a suitable dosage selected for therapy. The administration of this second reagent may occur simultaneously with the Chfr inhibitor composition, or the administration of the agent which disrupts microtubule function may occur at some time after the Chfr inhibitor has produced its effect on the tumor cells. This method is useful in some embodiments in killing the cancer cell.

This method may be performed by administering the pharmaceutical compositions described above via any suitable therapeutic route, and selection of such route is not a limitation of this invention. Similarly the appropriate dosage of such pharmaceutical compositions may be determined by a physician, based on typical characteristics such as the physical condition of the patient, the disease being treated, the use of other therapeutic compositions, etc. In one embodiment, the pharmaceutical compositions useful for practicing the therapeutic methods of the invention may be administered to deliver a dose of between 1 ng/kg/day and 100 mg/kg/day. The dosages of the agent which disrupts microtubule function, such as the TAXOL™ drug, are known to those of skill in the art. This invention is therefore not limited by the dosage selection, which is within the skill of the art.

E. Drug Screening and Screening for Chfr Inhibitors

The chfr nucleic acid sequences and Chfr polypeptides of this invention may also be used in the screening and development of chemical compounds, proteins or other compounds which have utility as therapeutic drugs for the treatment or diagnosis of cancer. Suitable assay methods for screening such potential drug compounds may be readily determined by one of skill in the art.

However, in one embodiment a method for identifying an inhibitor of chfr expression involves adding a test compound to a cell which is known to express Chfr at a specified level. The cell in which Chfr is expressed may be any cell found to express the chfr gene. Alternatively the cell may be one in which chfr is not normally expressed, but into which chfr has been introduced, by way of, for example, a plasmid or other vector, thereby enabling the expression of Chfr within the cell. After sufficient exposure to the test compound, the level of expression of chfr mRNA or protein is assessed according to the assays described in the examples below. This experimental level is then compared with the level of expression of chfr nucleic acid or Chfr protein in an otherwise identical cell to which the test compound has not been added. A lower level of expression of chfr nucleic acid or protein in a cell to which the test compound has been added, compared with the level in a cell to which the test compound has not been added, is an indication that the test compound is capable of inhibiting Chfr expression.

Inhibitors of Chfr activity may also be screened by resort to assays and techniques useful in identifying drugs capable of binding to or interacting with the Chfr polypeptide and thereby inhibiting its biological activity in a cell that expresses Chfr. For example, another method of identifying a Chfr inhibitor comprising the steps of screening a test compound in a Chfr-mediated ubiquitin-protein ligase assay, such as the in vitro assay described above and in Example 5 below and variants thereof. The substantial absence of, or reduction in, said ligase activity in the assay in the presence of said test compound indicates that said test compound inhibits Chfr function. In one embodiment, the Chfr-mediated ubiquitin-protein ligase in vitro assay may be performed to screen small chemical compounds as inhibitors. To develop or screen small chemical compounds that inhibit Chfr-mediated ubiquitin protein ligase activity, it is preferred to employ purified, recombinantly-produced labeled Chfr protein (e.g., glutathione S-transferase (GST)-Chfr), E1 and E2 enzymes. These proteins may be conventionally recombinantly produced in, e.g., bacterial cells, insect cells or any of the cells described above for recombinant production in section B above. This assay may be performed by contacting a mixture which normally demonstrates Chfr-mediated ubiquitin-protein ligase activity with a test compound; and assaying said mixture and test compound for said activity. This mixture can contain, among other things, a labeled Chfr protein, the E1 enzyme, the E2 enzyme, ubiquitin and ATP. The assay can include the further steps of separating said labeled Chfr protein from said mixture, and performing gel electrophoresis thereon. Immunoblotting said gel with an anti-ubiquitin antibody permits detection of ubiquitinated Chfr in the gel. Identification of the presence of ubiquitin on the Chfr protein by said antibody demonstrates Chfr-mediated ubiquitin-protein ligase activity. If the antibody cannot bind any ubiquitin in the gel, the cell has no functional Chfr. The performance of such an assay when the mixture is in the presence or, or absence of a test compound and the comparison of the results obtained identifies the test compound as a Chfr inhibitor. Similarly assays that measure the response of cells to mitotic stress, such as those described in Example 4 below may be used for screening of chemotherapeutic drugs according to this invention.

Other conventional drug screening techniques may be employed using the proteins, antibodies or polynucleotide sequences of this invention. As one example, a method for identifying compounds which specifically bind to a Chfr polypeptide of this invention can include simply the steps of contacting a selected cell expressing Chfr with a test compound to permit binding of the test compound to Chfr and determining the amount of test compound, if any, which is bound to the Chfr. Such a method may involve the incubation of the test compound and the Chfr polypeptide immobilized on a solid support. Typically, the surface containing the immobilized ligand is permitted to come into contact with a solution containing the protein and binding is measured using an appropriate detection system. Suitable detection systems include those described above for diagnostic use.

Thus, through use of such methods, the present invention is anticipated to provide compounds capable of interacting with Chfr or the chfr gene or portions thereof, and either enhancing or decreasing Chfr's biological activity, as desired. Such compounds are believed to be encompassed by this invention.

Still other methods of drug screening for novel compounds that inhibit chfr expression at the nucleic acid or protein level involve computational evaluation and design. According to these methods, the three dimensional structure of the chfr gene and/or the polypeptide is determined and chemical entities or fragments are screened and selected for their ability to associate with the three dimensional structures. Suitable software for such analysis include docking software such as Quanta and Sybyl, molecular dynamics and mechanics programs, such as CHARMM and AMBER, the GRID program available from Oxford University, Oxford, UK. [P. J. Goodford, *"A Computational Procedure for Determining Energetically Favorable Binding Sites on Biologically Important Macromolecules"*, *J. Med. Chem.*, 28:849–857 (1985)]; the MCSS program available from Molecular Simulations, Burlington, Mass. [A. Miranker and M. Karplus, *"Functionality Maps of Binding Sites: A Multiple Copy Simultaneous Search Method"*, *Proteins: Structure, Function and Genetics*, 11:29–34 (1991)]; the AUTODOCK program available from Scripps Research Institute, La Jolla, Calif. [D. S. Goodsell and A. J. Olsen, *"Automated Docking of Substrates to Proteins by Simulated Annealing"*, *Proteins: Structure, Function, and Genetics*, 8:195–202 (1990)]; and the DOCK program available from University of California, San Francisco, Calif. [I. D. Kuntz et al, *"A Geometric Approach to Macromolecule-Ligand Interactions"*, *J. Mol. Biol.*, 161:269–288 (1982)]. Additional commercially available computer databases for small molecular compounds include Cambridge Structural Database, Fine Chemical Database, and CONCORD database [for a review see Rusinko, A., *Chem. Des. Auto. News*, 8:4447 (1993)].

Once suitable chemical entities or fragments have been selected, they can be assembled into a single compound or Chfr inhibitor. Assembly may proceed by visual inspection of the relationship of the fragments to each other on the three-dimensional image displayed on a computer screen in relation to the 3D structure of Chfr. This would be followed by manual model building using software such as Quanta or Sybyl software, CAVEAT program [P. A. Bartlett et al, "CAVEAT: A Program to Facilitate the Structure-Derived Design of Biologically Active Molecules", in *Molecular Recognition in Chemical and Biological Problems"*, *Special Pub., Royal Chem. Soc.* 78, pp. 182–196 (1989)], which is available from the University of California, Berkeley, Calif.; 3D Database systems such as MACCS-3D database (MDL Information Systems, San Leandro, Calif.) [see, e.g., Y. C. Martin, "3D Database Searching in Drug Design", *J. Med.*

Chem., 35:2145–2154 (1992)]; and the HOOK program, available from Molecular Simulations, Burlington, Mass.

Other molecular modeling techniques may also be employed in accordance with this invention. See, e.g., N.C. Cohen et al, "Molecular Modeling Software and Methods for Medicinal Chemistry", *J. Med. Chem.*, 33:883–894 (1990). See also, M. A. Navia and M. A. Murcko, "The Use of Structural Information in Drug Design", *Current Opinions in Structural Biology*, 2:202–210 (1992). For example, where the structures of test compounds are known, a model of the test compound may be superimposed over the model of the structure of the invention. Numerous methods and techniques are known in the art for performing this step, any of which may be used. See, e.g., P. S. Farmer, *Drug Design*, Ariens, E. J., ed., Vol. 10, pp 119–143 (Academic Press, New York, 1980); U.S. Pat. No. 5,331,573; U.S. Pat. No. 5,500,807; C. Verlinde, *Structure*, 2:577–587 (1994); and I. D. Kuntz, *Science*, 257:1078–1082 (1992). The model building techniques and computer evaluation systems described herein are not a limitation on the present invention.

Thus, using these computer evaluation systems, a large number of compounds may be quickly and easily examined and expensive and lengthy biochemical testing avoided. Moreover, the need for actual synthesis of many compounds is effectively eliminated. Once identified by the modeling techniques, the Chfr inhibitor may be tested for bioactivity using the assays described herein.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLE 1

Identification and sequencing of chfr

To identify novel mitotic checkpoint genes, the Expressed Sequence Tag database was searched for cDNAs with FHA motifs. One of the positively identified cDNAs corresponded to EST clones #650972 and #1071323 and was sequenced in its entirety. See, e.g., FIGS. 4A–4D. The cDNA [SEQ ID NO: 1] encodes a 664 amino acid protein [SEQ ID NO: 2] that contains within its N-terminus FHA and ring finger domains [Lovering et al., 1993, *Proc. Natl. Acad. Sci. USA*, 90:2112–2116; Borden et al, 1995, *EMBO J.* 114:1532–1541; Hofmann, K. & Bucher, P *Trends Bioch. Sci.* 20, 347–349 (1995)]. Within its C-terminus is found a cysteine-rich region that is highly conserved between human and mouse, but which does not display significant similarity to any protein in the GenBank database, including the recognized zinc-binding domains (FIG. 1A). As described below, this protein functions as a mitotic cell cycle checkpoint. It is referred to herein as Chfr (CHeckpoint with FHA and Ring finger). Chfr may be a member of a small family of proteins that contain FHA and Ring Finger domains. Other members of this small family are Dma1 (Defective in mitotic arrest 1), an *S. pombe* mitotic checkpoint protein [Murone and Simanis, 1996, *EMBO J.*, 15:6605–6616], and Yhl115c and Ynl116w, the predicted protein products of two, as yet uncharacterized, *S. cerevisiae* open reading frames (FIG. 1A). Dma1, Yhl15c and Ynl116w are highly related to each other, whereas Chfr bears less similarity to these three proteins and may not be, therefore, their human ortholog (FIGS. 1A to 1C).

The FHA domain of Chfr has highest similarity to the FHA domain of Rad53/Spk1 (FIG. 1B), a DNA damage checkpoint protein kinase [Stem et al., 1991, *Mol. Cell. Biol.* 1:987–1001; Allen et al, 1994, *Genes Dev.*, 8:2401–2415], whereas the ring finger is most similar to the ring finger of the Varicella zoster virus transactivator ICP0 (FIG. 1C). Apart from its role as a transactivator [Moriuchi et al., 1992, *J. Virol.*, 66:7303–7308], ICP0 interacts with the kinetochore and interferes with progress through mitosis. These two activities require an intact ring finger [Everett et al., 1999, *EMBO J,* 118:1526–1538].

No proteins with significant similarity to the C-terminus of Chfr were identified.

EXAMPLE 2

Methods and Materials Employed in the Following Experiments

The materials and methods used in the experiments presented herein are now described.

A. Chfr Expression in Normal Tissues and Cancer Cell Lines

Chfr expression was examined at the mRNA and protein levels. For analysis at the mRNA level, a chfr probe corresponding to the Eco47III fragment of EST clone # 650972 was prepared by $^{32}$P-labeling (Oligolabeling Kit, Pharmacia, Piscataway, N.J.) and was hybridized with a human multiple tissue Northern blot (Clontech Inc., Palo Alto, Calif.) and Northern blots prepared with mRNA isolated from cancer cells lines using the Quickprep Micro mRNA Purification Kit (Pharmacia, Piscataway, N.J.). The extent of hybridization was monitored by autoradiography.

For analysis of expression of chfr protein, cells were recovered from tissue culture plates with trypsin, pelleted and lysed in cell lysis (CL) buffer (50 mM Tris, pH 8, 120 mM NaCl, 0.5% NP-40, 1 mM DTT, 1 µM staurosporine, 15 mM NaF, 1 mM sodium vanadate, 1 µg/ml aprotinin and 1 µg/ml leupeptin). The proteins in the whole cell lysates were resolved by denaturing gel electrophoresis and transferred to PVDF membranes. Immunoblotted Chfr protein was detected using an affinity-purified rabbit polyclonal antibody prepared using purified recombinant histidine-tagged Chfr protein as the antigen (Research Genetics).

B. Cell Culture

All cancer cells were grown in DMEM supplemented with glutamine, penicillin, streptomycin and 10% fetal bovine serum (Life Sciences). Normal human epidermal keratinocytes and osteoblasts were grown in KGM2 and OGM media, respectively (Clonetics). The cells were examined either non-synchronized or synchronized. For synchronization, the cells were treated with 2 mM thymidine for 16 hours, then with 0.25 mM thymidine/deoxycytidine for 9 hours, and then with 0.5 µg/ml aphidicolin for 20–24 hours. The cells were washed three times with PBS between each step [Janss et al., 1998, *Exp. Cell Res.*, 243:29–38]. To induce mitotic stress, synchronized or non-synchronized cells were exposed to 0.5 µg/ml nocodazole, 5 µM of the TAXOL™ drug or 0.5 µg/ml colcemid.

C. Ectopic Chfr Expression

The mammalian expression plasmid, pSV2-HAchfr, which directs expression of chfr in mammalian cells, was constructed from pSV2hp53BS by replacing the p53 insert with an insert encoding full-length Chfr protein fused at its N-terminus to an HA tag [Wieczorek et al., 1996, *Nature Med.*, 2:1143–1146]. pSV2-HAchfrV$_{580}$M (also pSV2-HAchfrM$_{580}$), which was derived from pSV2-HAchfr by site-directed mutagenesis, encodes a chfr protein bearing a substitution of $Val_{580}$ with Met. pSV2-HAchfr-ΔFHA was derived from pSV2-HAchfr by site-directed mutagenesis and lacks nucleotide residues 2–142 of chfr of FIGS. 4A–4D [SEQ ID NO: 1].

Stable transfectants were prepared by transfecting DLD1 or U20S cells with 5 μg pSV2-HAchfr or pSV2-HAchfr-$M_{580}$, or 5 μg pSV2 vector without insert and 1 μg pSV7neo plasmid [Wieczorek et al., supra] using Fugene-6 transfection reagent (Roche). Stably transfected cells were selected with G418. For transient expression, DLD1 or U20S cells were transfected with 5 μg pSV2-HAchfr or pSV2-HAchfrM$_{580}$ or pSV2 plasmid without insert and 2 μg of a plasmid expressing green fluorescent protein using Fugene-6. SAOS2 cells were transfected as described above, except that the plasmids expressing Chfr were cotransfected with a plasmid expressing green fluorescent protein (GFP).

D. Mitotic Index and Centrosome Staining

Cells were grown on 8-well culture slides coated with human fibronectin (Becton Dickinson) and were examined as either non-synchronized or synchronized cells. The cells were prepared for microscopy by washing them three times with KM buffer (10 mM MES, pH 6.2, 10 mM NaCl, 1.5 mM $MgCl_2$, 2.5% glycerol), fixing with 1% paraformaldehyde in 0.5×KM buffer for 15 minutes, washing once with 0.2% Triton X-100 in phosphate buffer saline (PBS) for 20 minutes and three times with PBS. For centrosome staining, the cells were incubated for 1 hour with a 1:500 dilution of autoimmune serum Ab598 in PBS, washed three times with PBS, incubated with a Texas Red-conjugated anti-human secondary antibody (Vector Labs) diluted 1:200 in PBS and washed again three times with PBS. For DNA staining, the cells were incubated with DAP1 (2 mg/ml in PBS). The slides were sealed with coverslips using Fluoromount-G (Upstate Biotechnology) and visualized with a fluorescence microscope (Leica). Separate images, acquired using filters corresponding to the excitation maxima of DAP1 and Texas Red, were merged with IRIX image tools (Silicon Graphics).

E. Determination of Viability in Response to Mitotic Stress

Cells synchronized by a sequential thymidine-aphidicolin block were either not exposed to mitotic stress or exposed to 0.5 μg/ml nocodazole or the TAXOL™ drug for a 4 hour period starting 12 hours after aphidicolin release or release from the G1-S block. The short term response to mitotic stress was evaluated by examining the cell cycle profile at the time of nocodazole removal, 24 or 48 hours later. At the indicated time points, the cells were recovered from the tissue culture plates with trypsin, fixed in 70% ethanol for 10 minutes and incubated with propidium iodide and DNase-free RNase (Roche) in PBS containing 1% fetal bovine serum and 2% Tween-20. The nuclear morphology of the cells was visualized by fluorescence microscopy. The DNA content of the cell population was determined by flow cytometry.

To evaluate the long term response of the cells to survive exposure to mitotic stress, at the time of nocodazole removal, the cells were replated at a density of 200 cells per 100 mm diameter tissue culture dish. The cells were allowed to replicate and colonies were counted 3 weeks later.

F. Cdc2 Kinase Activity

Whole cell extracts, prepared as described above, were incubated with anti-cyclin B antibody (Santa Cruz) coupled to protein G beads (Pharmacia) in CL buffer for 1 hour. The beads were washed three times with CL buffer and then twice with cdc2 kinase (CK) buffer (50 mM HEPES, pH 7.0, 10 mM $MgCl_2$, 10 mM $MnCl_2$, 200 mM NaCl). The beads were then incubated with 1 μg histone H1 (Upstate Biotechnology) in CK buffer supplemented with 30 mM DTT, 0.06 μM ATP and 1 μCi $^{32}$P-γ-ATP for 20 minutes at 30° C., at which time the reactions were subjected to denaturing gel electrophoresis. Phosphorylation of histone H1 was detected by autoradiography.

EXAMPLE 3

Detection of Chfr Mutations in Cancer Cell Lines

The following experiment was an examination of whether the chfr gene is mutated in any of the cancer cell lines (including SW480, DLD1, HT29, HCT116, SAOS2, U20S, IMR5 and NGP), e.g., those that express mRNA and protein or those that do not. Specifically examined was whether a mutation in chfr gene in a cancer cell line leads to synthesis of a functionally inactive protein. For this purpose, mRNA was isolated from these cancer cell lines (Quickprep Micro mRNA Purification Kit, Pharmacia) and was used as template for first-strand cDNA synthesis (Retroscript, Ambion). Synthetic oligonucleotides were used to amplify regions of the chfr cDNA by RT-polymerase chain reaction (Platinum Taq, Life Sciences or GC-rich PCR system, Roche). The amplified regions spanning the entire Chfr coding sequence were sequenced using four-color fluorescent dideoxy terminators (Big Dyes, Perkin Elmer). The oligonucleotides used to generate the PCR fragment served as sequencing primers. Specific primer pairs used to amplify regions of the chfr cDNA by PCR are reported in Table 1.

TABLE 1

| 5' Primer | SEQ ID NO | 3' Primer | SEQ ID NO | Region amplified [nts of SEQ ID NO: 1] |
|---|---|---|---|---|
| TGTCTCTTGACAGCGGC | 9 | CATGGAACACATTTTCCTTG | 10 | 66–562 |
| AAAGAATTCTGGAAGATACCAGCACCAG | 11 | AAAAAGCTTGGCAGATGATGCATGTCAG | 12 | 352–1055 |
| AAAGAATTCCTCCCCTAAAGGAAGTG | 13 | AAAAAGCTTTCAACGTCTGACAGCTC | 14 | 771–1376 |
| AAGAAAATGAGAGGAGATGG | 15 | GGTTGAGCTCACAAAACG | 16 | 904–1753 |
| AAGAAAATGAGAGGAGATGG | 17 | TCCAGACACTTGTCACC | 18 | 904–1772 |
| AAGAAAATGAGAGGAGATGG | 19 | AGACAGCAGAAACACTCC | 20 | 904–1902 |

TABLE 1-continued

| 5' Primer | SEQ ID NO | 3' Primer | SEQ ID NO | Region amplified [nts of SEQ ID NO: 1] |
|---|---|---|---|---|
| ACCACATCCTCAACAACC | 21 | GGTTGAGCTCACAAAACG | 22 | 1187–1753 |
| ACCACATCCTCAACAACC | 23 | TCCAGACACTTGTCACC | 24 | 1187–1772 |
| ATACCTCATCCAGCATCC | 25 | GGTTGAGCTCACAAAACG | 26 | 1215–1753 |
| ATACCTCATCCAGCATCC | 27 | TCCAGACACTTGTCACC | 28 | 1215–1772 |
| ATACCTCATCCAGCATCC | 29 | AGACAGCAGAAACACTCC | 30 | 1214–1902 |
| AAAGAATTCCAGCCTTTCTGCCACC | 31 | AAAAAGCTTTCCACAGAAGAGTCACCC | 32 | 1625–2279 |

Figure 3A:
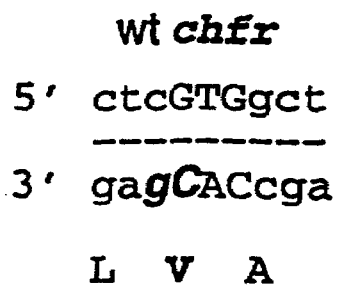
FIG. 3A illustrates the double-stranded nucleotide sequence of wild-type (wt) chfr [SEQ ID NO: 1] encoding amino acid residues $Leu_{579}$, $Val_{580}$ $Ala_{581}$ of SEQ ID NO: 2. The dinucleotide CG in the non coding strand is underlined and italicized. L, Leu; V, Val; A, Ala.
Figure 3B:
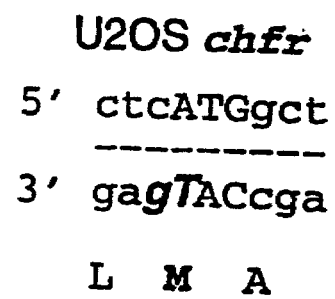
FIG. 3B illustrates the double-stranded nucleotide sequence of variant chfr cDNA from U20S cells [SEQ ID NO: 1] corresponding to amino acid residues 579–581 which bear a chfr missense mutation. The U20S sequence $Leu_{579}$ $Met_{580}$ $Ala_{581}$ of SEQ ID NO: 2 shows $Met_{580}$, not $Val_{580}$, as in wildtype. The relevant codon is underlined. The mutated dinucleotide mutation TG is underlined and italicized. L, Leu; M, Met; A, Ala.

Analysis of the sequences indicated that U2OS was the only cell line that displayed a sequence variation (see, FIGS. 3A and 3B). This experiment detected the presence of a C→T transition in the non-coding strand in Chfr cDNA prepared from U2OS cells, leading to substitution of $Val_{580}$ with $Met_{580}$ in the highly conserved C-terminal cysteine-rich region of Chfr and affecting the entire pool of U2OS mRNA. The sequencing did not reveal any wildtype sequence. The transition involves substitution of a CG dinucleotide (which is a mutagenesis hot-spot [Holliday, R. & Grigg, G. W., 1993, Mutat. Res., 285, 61–67]) in the non-coding strand with a TG dinucleotide and is typical of mutations that occur when methylated cytosines undergo deamination to form thymine [You et al., 1998, Mutation Res., 420:55–65]. Furthermore, the substitution targets a region of Chfr protein that is very highly conserved in evolution and was not detected in SW480 cells, which retain wild-type Chfr function.

EXAMPLE 4

Experiments and Results

Using the methods outlined in Example 2 above, the following data was collected and interpreted involving chfr and its biological function in regulating the response of cells to mitotic stress. As determined below, the correlation between Chfr expression and mitotic index in response to nocodazole is consistent with a role of Chfr as a cell cycle checkpoint.

In normal human tissues, expression at the mRNA level was determined by Northern blotting. In the resulting gels, Chfr expression was found in normal tissue of the heart, brain, placenta, lung, liver, muscle, kidney and pancreas. Thus, Chfr expression was ubiquitous in normal human tissues, providing evidence that its function is not tissue-specific.

Chfr expression was further examined in a panel of eight human cancer cell lines, including SW480, DLD1, HT29, HCT116, SAOS2, U2OS, IMR5 and NGP. At the mRNA level, three of the eight cell lines did not express detectable chfr (DLD1, HCT116 and IMR5). Expression at the protein level was also determined by Western immunoblotting with an affinity-purified polyclonal antibody raised against recombinant Chfr protein. The cell lines DLD1, HCT116 and IMR5 did not express Chfr protein. The molecular basis for the lack of Chfr expression does not involve deletion of both copies of the chfr gene, since by Southern blotting all eight of the above-mentioned cancer cell lines have at least one copy of the chfr gene. Nevertheless, the high frequency of undetectable Chfr expression prompted an examination of whether chfr is mutated in these cancer cell lines, including those that express mRNA and protein, as described in Example 3 above.

Figure 2:
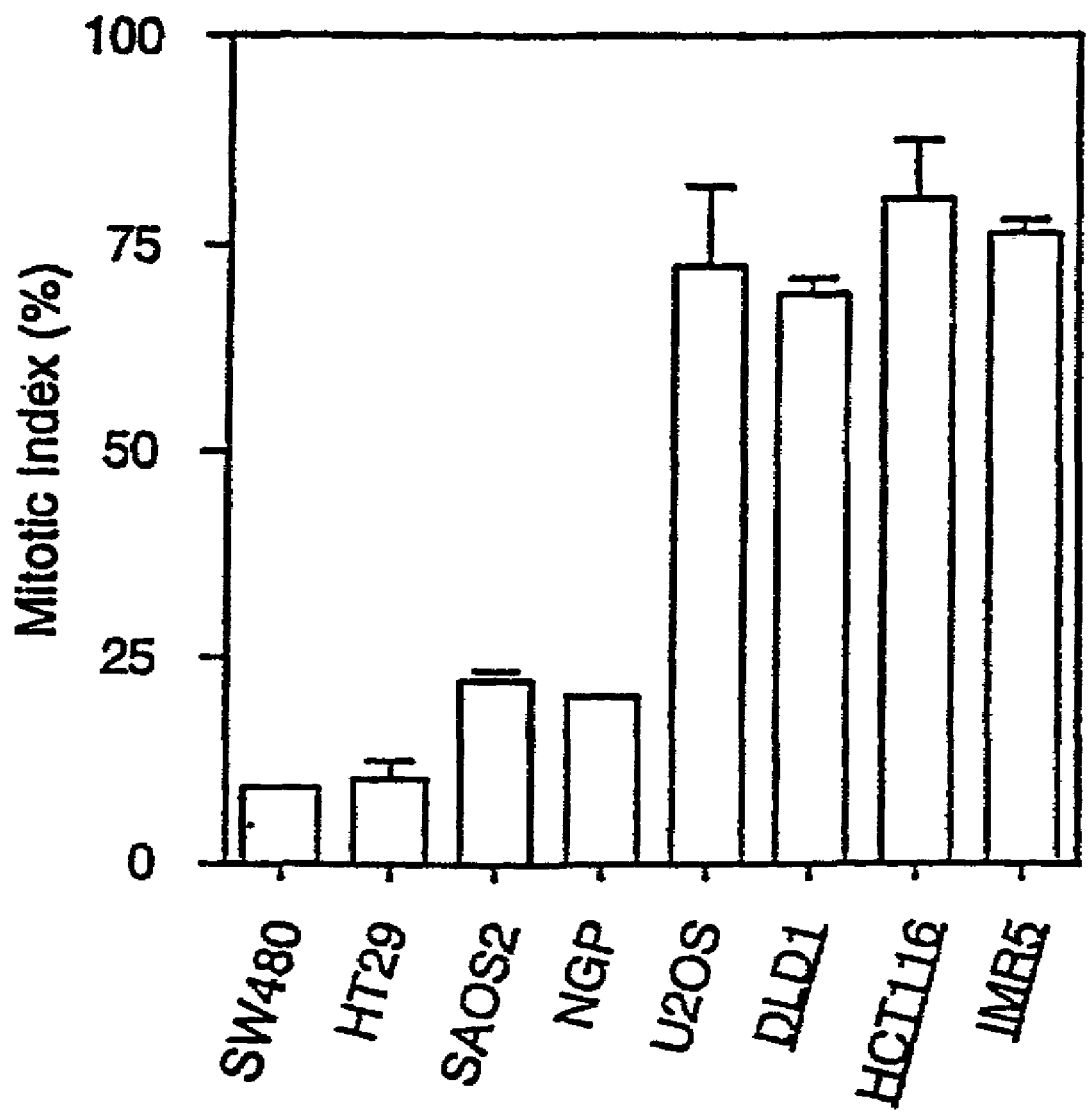
FIG. 2 is a graph illustrating the mitotic index of unsynchronized human tumor cell lines exposed to nocodazole for 16 hours, demonstrating the fact that chfr regulates the response of cells to mitotic stress. The names of the cell lines that do not express chfr are underlined.

Because Chfr and Dma1 share structural domains, the possibility that chfr is a mitotic checkpoint gene was examined. The eight cancer cell lines described above were treated with nocodazole, which induces mitotic stress by depolymerizing the microtubules that form the mitotic spindle. The ability of cells to undergo mitotic arrest was examined by staining the cells with DAPI 16 hours later. The cells were scored for Mitotic Index. Mitotic index is the fraction of cells that had condensed chromosomes, and represents cells that are in metaphase or anaphase. For the cell lines that had no detectable Chfr expression and for the U2OS cells, which expressed the variant chfr gene, the fraction of cells that had condensed chromosomes (mitotic index) was high, indicating arrest in metaphase. In contrast, the mitotic index of the cell lines that expressed wild-type Chfr was low (FIG. 2), which indicates either that these cells were not arrested in the cell cycle or that they were arrested in some phase of the cell cycle other than metaphase or anaphase.

Figure 3C:
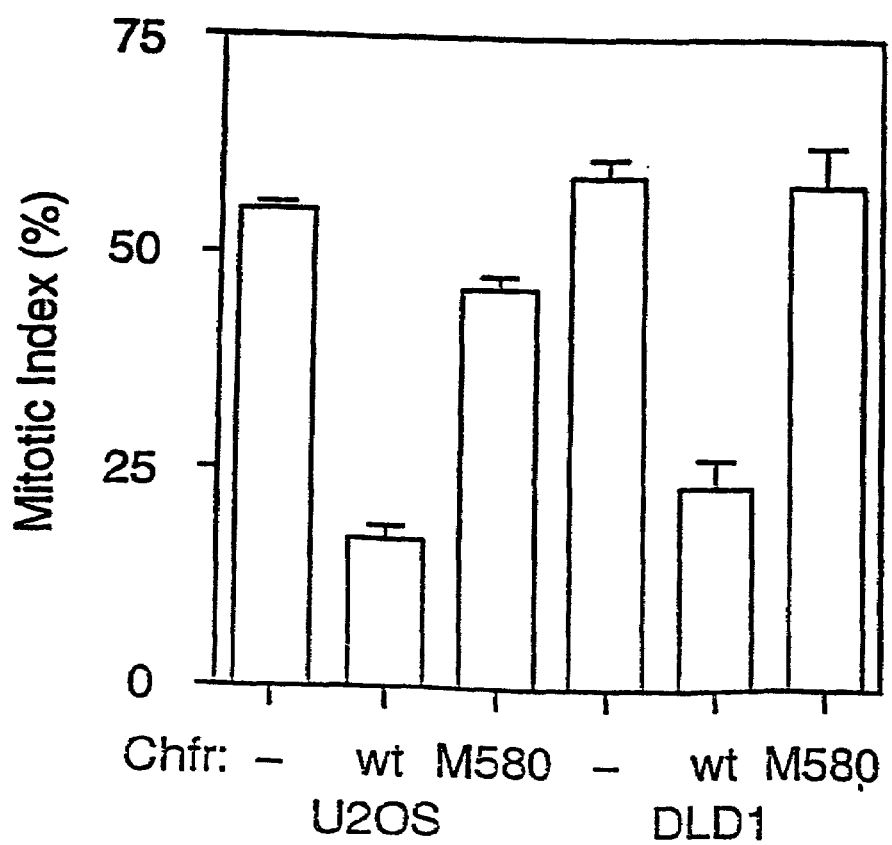
FIG. 3C is a bar graph depicting the mitotic index of unsynchronized U20S and DLD1 cells transiently-transfected with plasmids expressing wild-type (wt) or mutant ($Met_{580}$) chfr in response to nocodazole treatment for 16 hours.
Figure 7A:
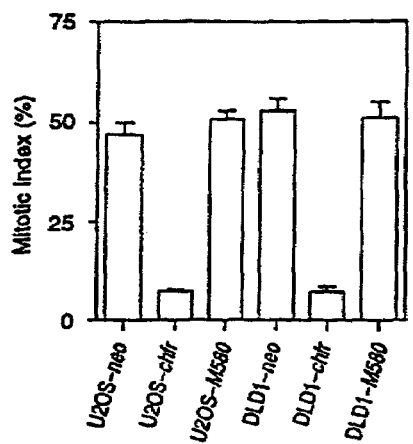
FIG. 7A is a bar graph illustrating the mitotic index of unsynchronized U20S and DLD 1 cells stably transfected with plasmids expressing neo or wildtype chfr or chfr-$M_{580}$ after exposure to nocodazole for 16 hours.

To determine whether Chfr accounted for the different response, DLD1 and U2OS cells were prepared to stably express HA-tagged wild-type Chfr or Chfr with the $Val_{580}$ to Met substitution ($M_{580}$) or just the neo selectable marker. The cells expressing neo or Chfr-$M_{580}$ had a high mitotic index in response to nocodazole, like the parent cells. However, the cells expressing wild-type Chfr had a low mitotic index (FIG. 7A). Near normal levels of wild-type Chfr protein were sufficient to affect the response to mitotic stress, since the ectopic Chfr protein in the stably-transfected DLD1-chfr cells was expressed at levels similar to those of endogenous Chfr in primary human cells (NHEK, NHOST and NHF; obtained from Clonetics). Furthermore, the different effects of wild-type Chfr and Chfr-$M_{580}$ could not be attributed to differences in protein expression, as determined by immunoblotting. Similar results were obtained with transiently transfected U2OS and DLD1 cells (FIG. 3C). Thus the nucleotide transition targeting chfr in U2OS cells is a mutation, because it inactivates the function of Chfr.

To further strengthen the link between Chfr and the response to mitotic stress, experiments were performed to determine whether a dominant negative Chfr mutant would alter the behavior of cells, such as SAOS2, that express wild-type Chfr and have a low mitotic index in response to mitotic stress. Chfr-ΔFHA, a Chfr protein with deletion of residues 2–142 encompassing the FHA domain, was identified as a dominant negative mutant by studying its function in DLD 1 cells. Its effect on the response of SAOS2 cells to mitotic stress was studied by transiently-transfecting these cells with plasmids that express Chfr-ΔFHA or wild-type Chfr or no Chfr protein, together with a plasmid expressing GFP, as a marker. 36 hours later, mitotic stress was induced by exposure to the TAXOL™ drug and the mitotic index was determined 8 to 16 hours late. Protein levels were determined by immunoblotting with an antibody that recognizes the N-terminal HA tag of the expressed Chfr proteins.

Figure 7B:
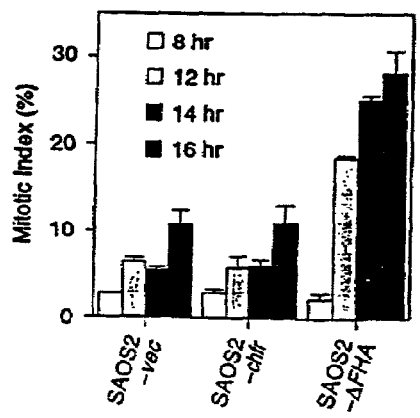
FIG. 7B is a bar graph showing mitotic index of unsynchronized SAOS2 cells transiently-transfected with plasmids expressing no Chfr protein (vec), wild-type Chfr or ChfrΔFHA. The TAXOL™ drug was added 36 hours after the transient transfection and the mitotic index was determined 8 (white bar), 12 (gray bar), 14 (first black bar) and 16 (second black bar) hours later.
Figure 7C:
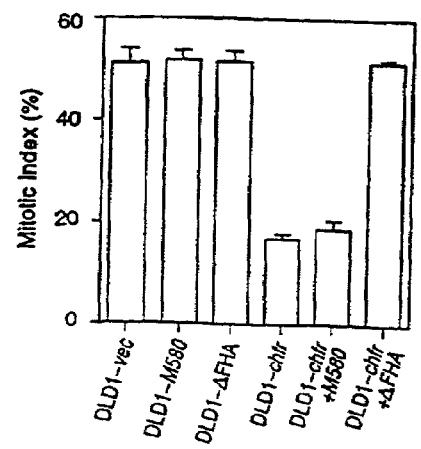
FIG. 7C is a bar graph illustrating the mitotic index of unsynchronized DLD 1 cells transiently-transfected with plasmids expressing no Chfr protein (DLD1-vec), wild-type Chfr (DLD-chfr; 1 µg), ChfrMet$_{580}$ (DLD1-M$_{580}$; 5 µg), ChfrΔFHA (DLD1-ΔFHA; 5 µg), or wild-type Chfr (1 µg) and ChfrM$_{580}$ (5 µg) (DLD1-chfr+M$_{580}$), or wild-type Chfr (1 µg) and ChfrΔFHA (5 µg) (DLD1-chfr+ΔFHA). The TAXOL™ drug was added 36 hours after the transient transfection and the mitotic index was determined 16 hours later.

About 50% of the cells expressed GFP, but the variable level of expression made it difficult to define a threshold above which a cell would be considered GFP-positive. Thus, to avoid any bias, the mitotic index was calculated for the entire cell population. Expression of wild-type Chfr had no effect as compared to cells transfected with empty vector (FIG. 7B). However, Chfr-ΔFHA, whose level of expression was equivalent to that of wild-type Chfr led to a five-fold increase in the mitotic index at the 12, 14 and 16 hour timepoints, indicating a checkpoint defect. At the 8 hour timepoint, the mitotic index was low, similar to cells that lack Chfr (e.g. DLD 1 and HCT 116), which begin to show a high mitotic index in response to mitotic stress 12–16 hours after addition of nocodazole or the TAXOL™ drug. The effect of Chfr-ΔFHA in this assay was through dominant inhibition of endogenous wild-type Chfr based on an analysis of its function in transiently-transfected DLD1 cells, which lack endogenous Chfr. Chfr-ΔFHA had no effect on the mitotic index of DLD 1 cells exposed to mitotic stress, as compared to vector control, but inhibited the ability of wild-type Chfr to decrease the mitotic index. In the same assay, Chfr-$M_{580}$ aid not act as a dominant negative mutant (FIG. 7C).

The low mitotic index of nocodazole-treated cells expressing wild-type Chfr could indicate either cell cycle arrest at some point in the cell cycle before entry into metaphase or due to exit from mitosis due to failure to arrest in metaphase. To distinguish between these possibilities, the effect of Chfr expression in synchronized cells was examined. The stably-transfected DLD1-chfr and DLD 1-neo cells described above were synchronized by consecutive thymidine and aphidicolin blocks at the G1-S boundary. Aphidicolin was then washed off. These cells were allowed to proceed through the cell cycle (mitosis) either in the presence or absence of mitotic stress (i.e., the cells were either treated with nocodazole 12 hours after release from cell cycle arrest or not exposed to nocodazole). Progression through the cell cycle was monitored by measuring the mitotic index and by flow cytometric analysis of the DNA content of the cells.

In the absence of nocodazole (i.e., mitotic stress), Chfr had no effect on cell cycle progression, including entry and exit from mitosis, as determined by analysis of the mitotic index and cdc2 kinase activity performed as described in Example 2, and measured as a function of time after release from aphidicolin-induced cell cycle arrest. However, Chfr delays entry into metaphase in response to mitotic stress (FIGS. 8A and 8B).

Figure 8A:
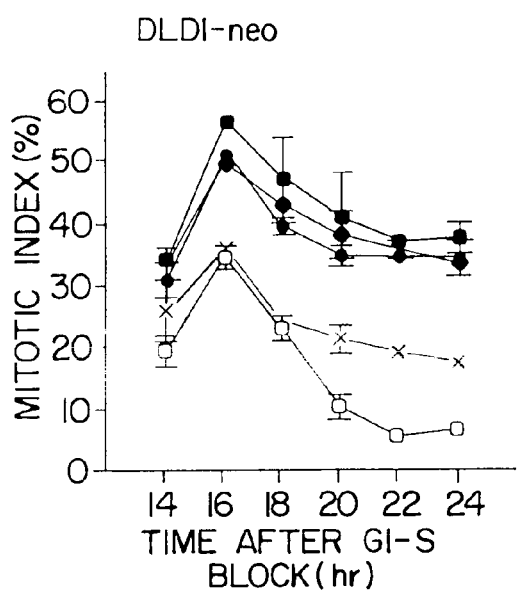
FIG. 8A is a graph showing mitotic index of synchronized DLD1 cells stably-transfected with plasmids expressing neo (DLD1-neo) as a function of time in hours after release from the G1-S block. The cells were either not exposed to mitotic stress (□) or treated with nocodazole (■), the TAXOL™ drug (•) or colcemid (♦) 12 hours after release from the cell cycle block or treated with nocodazole (X) 14 hours after release.
Figure 8B:
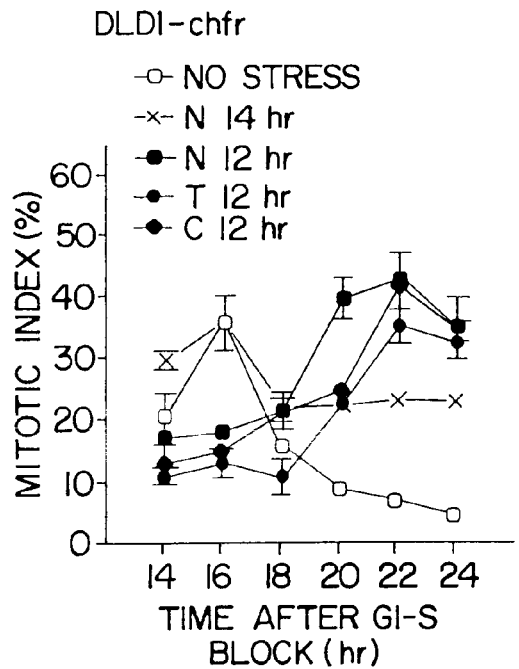
FIG. 8B is a graph showing mitotic index of synchronized DLD 1 cells stably-transfected with plasmids expressing chfr (DLD 1-chfr) as a function of time after release from the G1-S block. The cells were treated as described for FIG. 8A (symbols are identical).
Figure 8C:
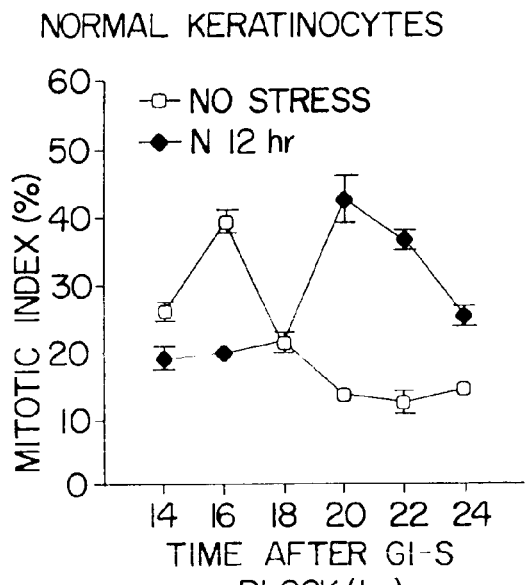
FIG. 8C is a graph showing mitotic index of synchronized normal (primary) human epidermal keratinocytes in the absence (□) and presence of mitotic stress induced with nocodazole, N, 12 hours after release from the G1-S block (♦).
Figure 8D:
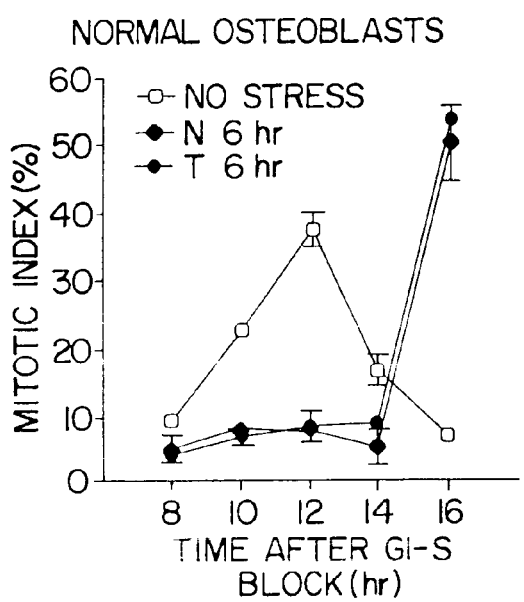
FIG. 8D is a graph showing mitotic index of synchronized normal (primary) human osteoblasts in the absence (□) and presence of mitotic stress induced by the TAXOL™ drug, T, (●) or nocodozole, N, (♦) 6 hours after release from the G1-S block.

Similar results were obtained when mitotic stress was induced by colcemid or the TAXOL™ drug, two other drugs that affect microtubule dynamics (FIGS. 8A and 8B). Thus, Chfr regulates the prophase to metaphase transition in response to mitotic stress. Consistent with this role, the timing of induction of mitotic stress was critical for Chfr to delay entry in metaphase. Chfr did not affect cell cycle progression when nocodazole was added as the cells were entering metaphase 14 hours after aphidicolin release. In this case, both DLD1-neo and DLD1-chfr cells arrested in metaphase or entered metaphase with the same kinetics, as in the absence of mitotic stress (see, e.g., FIGS. 8A and 8B). Essentially identical results were obtained when U20S cells stably-transfected with plasmids expressing neo or wild-type chfr were examined. Furthermore, human primary epidermal keratinocytes and osteoblasts also exhibited a delay in metaphase entry in response to mitotic stress (FIGS. 8C and 8D).

To correlate the timing of the Chfr effect with progress through the cell cycle, synchronized cells were stained with DAP1 to monitor chromosome condensation and with an antibody that recognizes the centrosomes. A series of images was generated depicting disjunction of chromosome condensation and centrosome separation in cells lacking Chfr. Representative views of DLD1-neo and DLD1-chfr cells at 12, 14 and 16 hours after release from aphidicolin arrest were generated. DNA was stained with DAP1 and centrosomes were identified by immunofluorescence. At 12 hours after aphidicolin release, the nucleus exhibited no signs of chromosome condensation and the centrosomes, which duplicate in S phase, were physically next to each other, suggesting that the cells were in G2. At 14 hours, most of the cells were in prophase since the centrosomes had separated from each other, while the chromosomes had not yet condensed. At 16 hours, most of the cells were in metaphase with condensed chromosomes between the separated centrosomes.

Representative views of DLD1-neo and DLD1-chfr cells at the 14 hour time point after release from aphidicolin arrest were also generated. These cells were exposed to nocodazole 12 hours after release from cell cycle arrest. When nocodazole was added 12 hours after aphidicolin release, centrosome separation at the 14 hour time point was inhibited in both DLD1-chfr and DLD1-neo cells. At this time point, a significant number of DLD1-neo cells had condensed chromosomes despite failing to separate their centrosomes, whereas the DLD1-chfr cells typically did not exhibit chromosome condensation.

Cyclin B/cdc2 activity was high in synchronized DLD1-neo and DLD1-chfr cells treated with nocodazole 12 hours after release from the G1-S block. Persistence of high cyclin B/cdc2 activity indicates arrest in mitosis; DLD1-neo cells were arrested in metaphase due to activation of the spindle checkpoint; DLD1-chfr cells were arrested initially in prophase by the Chfr checkpoint and later in metaphase by the spindle checkpoint (FIGS. 8A and 8B). The high cyclin B/cdc2 activity in cells whose entry into metaphase is delayed by Chfr distinguishes the Chfr checkpoint from the G2 DNA damage checkpoint, which delays entry into mitosis by inhibiting cyclin B/cdc2 [Weinert, T. 1998 *Cell* 94:555–558].

The ability of Chfr to affect progression through the cell cycle only in the presence of mitotic stress provides evidence that Chfr is a mitotic checkpoint. Furthermore, Chfr has an effect only when nocodazole was added prior to completion of prophase, which suggests that Chfr monitors events that occur during prophase. The nature of the event being monitored is likely centrosome separation. The disjunction of chromosome condensation from centrosome separation in the absence of the Chfr checkpoint is theorized to lead to aberrant chromosome segregation during anaphase and, consequently, to decreased cell viability.

To further support the hypothesis that Chfr is a mitotic checkpoint, Chfr was examined to determine whether it affects cell viability in response to mitotic stress. Stably-transfected DLD1-neo and DLD1-chfr cells were synchronized by sequential thymidine-aphidicolin blocks and exposed to 0.5 µg/ml nocodazole or the TAXOL™ drug for a 4 hour period starting 12 hours after aphidicolin release or release from the G1-S block. The short-term response of the cells to mitotic stress was evaluated by examining cellular DNA content by flow cytometry and their nuclear morphology under the fluorescent microscope 48 hours later and the cell cycle profile at the time of nocodazole removal, 24 or 48 hours later. For microscopic examination, the cells were recovered from the tissue culture plates with trypsin, fixed in 70% ethanol for 10 minutes and incubated with propidium iodide and DNase-free RNase (Roche) in PBS containing 1% fetal bovine serum and 2% Tween-20. Further, after staining the cells with DAP1, the cells were inspected by fluorescence microscopy 64 hours after release from G1-S block.

The DLD1-chfr cells exhibited the normal DNA content profile of cycling cells and normal nuclear morphology. The DNA content profile of the DLD1-neo cells was also normal, but their nuclear morphology was clearly aberrant. About half of all cells with a 4N DNA content exhibited fragmented nuclei suggesting that they had not completed mitosis properly.

Figure 5:
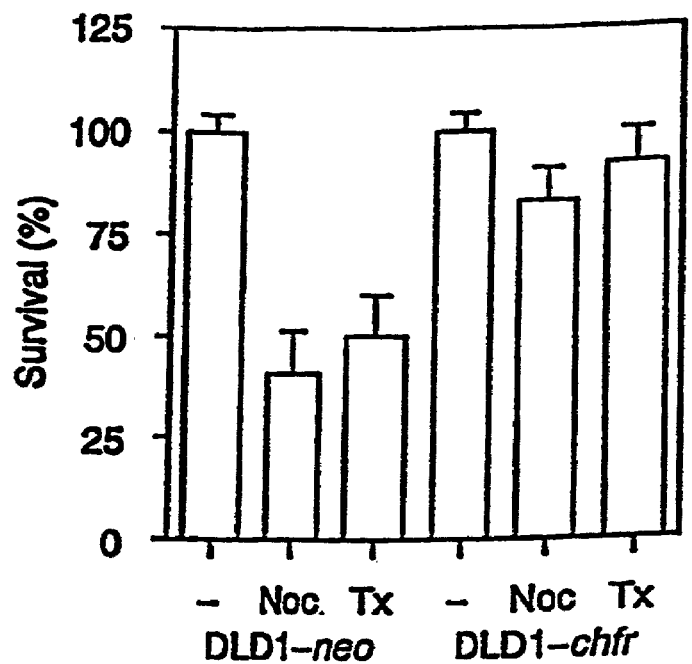
FIG. 5 is a bar graph showing the "long-term" response of synchronized DLD1-neo and DLD1-chfr cells exposed transiently to mitotic stress, e.g., to nocodazole (Noc) or the TAXOL™ drug (T) 12 hours after release from the G1-S block for a 4 hour period. The cells were replated and scored for colony formation 3 weeks later. The controls are indicated by (−).

To the long term response of the cells to survive exposure to mitotic stress, synchronized DLD1-neo and DLD1-chfr cells were transiently exposed to nocodazole or the TAXOL™ drug, as described above (e.g., exposed to nocodazole or the TAXOL™ drug 12 hours after release from the G1-S block for a 4 hour period). At the time of nocodazole removal, the cells were replated at a density of 200 cells per 100 mm diameter tissue culture dish and then allowed to form colonies over a three-week period. DLD1-neo cells showed a decrease in the number of colony-forming units (CFUs) in response to mitotic stress, whereas for the DLD1-chfr cells the number of CFUs was unaffected by mitotic stress (FIG. 5). This provides additional evidence that Chfr expression leads to a low mitotic index in response to nocodazole.

The chfr gene molecularly defines the existence of a novel checkpoint that regulates entry into metaphase. The Chfr checkpoint was evident in primary human cells, but was inactivated in four out of eight examined human cancer cell lines. In the absence of the Chfr checkpoint, cells subjected to mitotic stress condensed their chromosomes despite failing to separate their centrosomes. It is presently theorized that Chfr monitors centrosome separation, rather than some other mitotic stress-sensitive event that occurs in prophase. The molecular mechanism by which Chfr delays cell cycle progression and the frequency of Chfr inactivation in primary tumors are being studied. Analysis of a small number of cancer cell lines raises the possibility that Chfr is inactivated more frequently than all known spindle checkpoint genes combined. If Chfr is inactivated in human cancer, then its inactivation may underlie the increased sensitivity of cancer cells to antimitotic drugs.

EXAMPLE 5

Chfr has Ubiquitin-Protein Ligase Activity

Recombinant *E. coli* bacterial cells that have been genetically engineered to express the E1 ubiquitin-activating enzyme and the E2 ubiquitin-conjugating enzyme (either UbchD2 or Ubch8) and a fission protein comprised of glutathione S-transferase fused to the N-terminus of Chfr were lysed. The lysates were incubated in the presence of ubiquitin and ATP and the reaction allowed to proceed for 20 minutes at 30° C. GST-Chfr was captured on glutathione beads, eluted with SDS sample buffer, and resolved by SDS-PAGE. The SDS gel was immunoblotted with antibodies that recognize ubiquitin. Reactions were performed with full-length Chfr fused to GST and reactions were performed with Chfr lacking amino acid residues 1–280 of SEQ ID NO: 2, which contain the FHA domain. If the GST-Chfr is ubiquitinated, then the anti-ubiquitin antibodies will recognize the GST-Chfr protein, indicating that the GST-Chfr has ubiquitin-protein ligase activity.

Using this ubiquitin-protein ligase assay in vitro, efficient ubiquitination of GST-Chfr was detected (data not shown). As with other E3 ligases, ubiquitination required the presence of both E1 and E2 and demonstrated E2-specificity, since the E2 ubiquitin-conjugating enzyme UbchD2, supported the ubiquitin-protein ligase activity of Chfr, whereas another E2, Ubch8, did not function in this assay. The E3 ligase activity of Chfr was dependent on the integrity of its ring finger, since substitution of $CyS_{325}$ with Ala, abrogated ligase activity. In contrast, the FHA domain of Chfr was not required for ligase activity in vitro, since a GST-Chfr protein that lacks amino acid residues 1–280 of human Chfr [SEQ ID NO: 2], was active. Finally, GST by itself did not have ubiquitin-protein ligase activity in this assay.

These preliminary results were performed with crude bacterial lysates. However, all the recombinant proteins in these extracts could be visualized by Coomassie blue staining. The levels of expression of UbchD2 and Ubch8 were similar, as were the levels of all the GST-Chfr fusion proteins. Thus, the different activities observed with these different proteins were not simply due to differences in the levels of protein expression.

Figure 6:
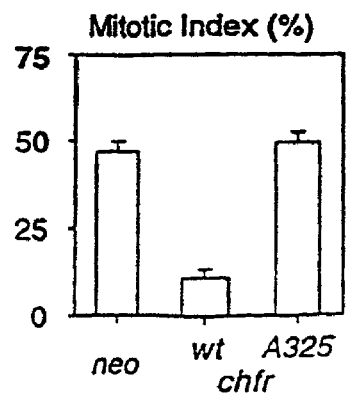
FIG. 6 is a bar graph showing the mitotic index of unsynchronized DLD1 cells stably transfected with plasmids expressing neo or wild-type Chfr or Chfr-$A_{325}$ after exposure to nocodazole for 16 hours.

To determine whether ubiquitin-protein ligase activity is required for checkpoint function, the Chfr mutant that substitutes $Cys_{325}$ of the ring finger with Ala was stably-expressed in DLD1 cells. These cells were then exposed to mitotic stress and examined for entry into metaphase. The mitotic index of unsynchronized DLD1 cells exposed to nocodazole is high, indicating the absence of a checkpoint that would delay entry into metaphase in response to mitotic stress. Expression of wild-type Chfr restores the checkpoint leading to a low mitotic index. Expression of $Chfr-A_{325}$, which lacks ubiquitin-protein ligase activity, did not lead to a low mitotic index (see FIG. 6) indicating that the checkpoint function of Chfr is dependent on its E3 ligase activity. Expression of $Chfr-A_{325}$ in the transfected DLD1 cells was monitored by immunoblotting and was shown to be equivalent to the expression of wild-type Chfr.

The chfr gene molecularly defines the existence of a novel checkpoint that regulates entry into metaphase. The Chfr checkpoint was evident in primary human cells; but was inactivated in four out of eight examined human cancer cell lines. In the absence of the Chfr checkpoint, cells subjected to mitotic stress condensed their chromosomes despite failing to separate their centrosomes. It is presently theorized that Chfr monitors centrosome separation, rather than some other mitotic stress-sensitive event that occurs in prophase. The molecular mechanism by which Chfr delays cell cycle progression and the frequency of Chfr inactivation in primary tumors are being studied. So far, analysis of a small number of cancer cell lines raises the possibility that chfr is inactivated more frequently than all known spindle checkpoint genes combined. The inactivation of chfr in human cancer is theorized to underlie the increased sensitivity of cancer cells to antimitotic drugs.

The disclosures of each and every patent, patent application, and publication cited herein, including that of provisional U.S. patent application No. 60/146,194 are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleotide sequence that encodes a Chfr polypeptide SEQ ID NO: 2 that delays entry of a human cell into metaphase in response to mitotic stress.

2. The nucleotide sequence according to claim 1, comprising
   (a) SEQ ID NO: 1 or
   (b) the complete complement of SEQ ID NO: 1.

3. The nucleotide sequence according to claim 2, which is synthetically or recombinantly produced.

4. The nucleotide sequence according to claim 2, which encodes SEQ ID NO: 2 in normal human epidermal keratinocytes and normal human osteoblasts.

5. A reagent consisting of a nucleic acid fragment of the protein-encoding sequence of SEQ ID NO: 1 or a nucleic acid fragment of the complete full-length complement of the protein-encoding sequence of SEQ ID NO: 1, wherein said fragment consists of between 12 to 30 nucleotides in length.

6. A kit for detecting expression of a nucleotide sequence encoding the Chfr protein SEQ ID NO: 2 in mammalian cells, said kit comprising
   (i) a first nucleic acid fragment of the coding sequence of SEQ ID NO: 1 consisting of between 12 to 30 nucleotides in length; and
   (ii) a second nucleic acid fragment of the complete full-length complement of the coding sequence of SEQ ID NO: 1 consisting of between 12 to 30 nucleotides in length.

7. A composition comprising a pair of primer sequences, said primer sequences consisting of
   (a) a fragment of the coding sequence of the nucleic acid sequence encoding Chfr protein of SEQ ID NO: 2 consisting of between 12 to 30 nucleotides in length; and
   (b) a fragment of the complete full-length complement of the coding sequence of the nucleic acid sequence encoding Chfr protein of SEQ ID NO: 2 consisting of between 12 to 30 nucleotides in length.

8. The reagent according to claim 5, further comprising a detectable label.

9. The reagent according to claim 8, wherein said label is a fluorescent label or an enzyme.

10. The reagent according to claim 5, wherein said nucleic acid sequence encodes an amino acid fragment from within amino acids 31–103 of SEQ ID NO: 2.

11. The reagent according to claim 5, wherein said nucleic acid sequence encodes an amino acid fragment from within amino acids 303 to 346 of SEQ ID NO: 2.

12. The reagent according to claim 5, wherein said nucleic acid sequence encodes an amino acid fragment from within amino acids 476 to 641 of SEQ ID NO:2.

13. The kit according to claim 6, wherein said nucleotide fragment (i) or (ii) is attached to a detectable label.

14. The kit according to claim 13, wherein said detectable label is a fluorescent compound or an enzyme.

15. The kit according to claim 14, further comprising one or more components that detect said labels.

16. The kit according to claim 6, further comprising a component selected from the group consisting of instructions for performing a PCR assay for the detection of the expression of a nucleotide sequence encoding Chfr polypeptide SEQ ID NO: 2, microtiter plates to which said nucleic acid sequences have been pre-adsorbed, diluents, buffers, applicator sticks, containers, and sample preparator cups.

17. The kit according to claim 6, wherein said nucleotide sequence (i) or (ii) is synthetically or recombinantly produced.

18. The kit according to claim 6, further comprising instructions for performing PCR.

19. The composition according to claim 7, wherein said nucleotide sequence encoding Chfr is SEQ ID NO: 1.

20. The composition according to claim 7, wherein said primers amplify a portion of the coding sequence of said nucleotide sequence encoding Chfr.

21. The composition according to claim 20, wherein said amplified portion is selected from the group consisting of, nucleotides 352–1055 of SEQ ID NO: 1, nucleotides 771–1376 of SEQ ID NO: 1, nucleotides 904–1753 of SEQ ID NO: 1, nucleotides 904–1772 of SEQ ID NO: 1, nucleotides 904–1902 of SEQ ID NO: 1, nucleotides 1187–1753 of SEQ ID NO: 1, nucleotides 1187–1772 of SEQ ID NO: 1, nucleotides 1215–1753 of SEQ ID NO: 1, nucleotides 1215–1772 of SEQ ID NO: 1, and nucleotides 1214–1902 of SEQ ID NO: 1.

22. The composition according to claim 20, wherein said amplified portion is selected from the group consisting of a nucleotide sequence encoding amino acids 31–103 of SEQ ID NO: 2; a nucleotide sequence encoding amino acids 303–346 of SEQ ID NO: 2; and a nucleotide sequence encoding amino acids 476–641 of SEQ ID NO: 2.

23. The composition according to claim 20, wherein said amplified nucleotide sequence is selected from the group consisting of nucleotides 180–399, nucleotides 557 to 1128 and nucleotides 1516–2013 of SEQ ID NO: 1.

* * * * *

UNITED STATES PATENT AND TRADEMARK OFFICE
CERTIFICATE OF CORRECTION

| | |
|---|---|
| PATENT NO. | : 7,176,293 B1 |
| APPLICATION NO. | : 10/048046 |
| DATED | : February 13, 2007 |
| INVENTOR(S) | : Halazonetis et al. |

It is certified that error appears in the above-identified patent and that said Letters Patent is hereby corrected as shown below:

Col. 1 (Lines 3 and 4) Insert

-- This invention was made with government support under National Institutes of Health Grant No. CA089630, awarded by the US Department of Health and Human Services. The government has certain rights in the invention. --

Signed and Sealed this

Fifteenth Day of July, 2008

JON W. DUDAS
*Director of the United States Patent and Trademark Office*

SEQUENCE LISTING

<160> NUMBER OF SEQ ID NOS: 32

<210> SEQ ID NO 1
<211> LENGTH: 2679
<212> TYPE: DNA
<213> ORGANISM: Homo sapiens
<220> FEATURE:
<221> NAME/KEY: CDS
<222> LOCATION: (91)..(2082)

<400> SEQUENCE: 1

```
aagaattcgg cacgaggccg caatgtctct tgacagcggc ggcggcgcag ccggttccgg      60
gttcggcgcg gggcggggat gtgaatcccg atg gag cgg ccc gag gaa ggc aag     114
                                 Met Glu Arg Pro Glu Glu Gly Lys
                                  1               5 cag tcg ccg ccg ccg cag ccc tgg gga cgg ctc ctg cgt ctg ggc gcg     162
Gln Ser Pro Pro Pro Gln Pro Trp Gly Arg Leu Leu Arg Leu Gly Ala
     10                  15                  20 gag gag ggc gag ccg cac gtc ctc ctg agg aag cgg gag tgg acc atc     210
Glu Glu Gly Glu Pro His Val Leu Leu Arg Lys Arg Glu Trp Thr Ile
 25                  30                  35                  40 ggg cgg aga cga ggt tgc gac ctt tcc ttc ccc agc aat aaa ctg gtc     258
Gly Arg Arg Arg Gly Cys Asp Leu Ser Phe Pro Ser Asn Lys Leu Val
                 45                  50                  55 tct gga gat cac tgt aga att gta gtg gat gaa aaa tca ggt cag gtg     306
Ser Gly Asp His Cys Arg Ile Val Val Asp Glu Lys Ser Gly Gln Val
             60                  65                  70 aca ctg gaa gat acc agc acc agt gga aca gtg att aac aag ctg aag     354
Thr Leu Glu Asp Thr Ser Thr Ser Gly Thr Val Ile Asn Lys Leu Lys
         75                  80                  85 gtt gtt aag aag cag aca tgc cct tta cag act ggg gat gtc atc tac     402
Val Val Lys Lys Gln Thr Cys Pro Leu Gln Thr Gly Asp Val Ile Tyr
     90                  95                 100 ttg gtg tac agg aag aat gaa ccg gaa cac aac gtg gca tac ctc tat     450
Leu Val Tyr Arg Lys Asn Glu Pro Glu His Asn Val Ala Tyr Leu Tyr
105                 110                 115                 120 gaa tct tta agt gaa aag caa ggc atg aca caa gaa tcc ttt gaa gct     498
Glu Ser Leu Ser Glu Lys Gln Gly Met Thr Gln Glu Ser Phe Glu Ala
                125                 130                 135 aac aag gaa aat gtg ttc cat ggg acc aaa gat acc tca ggt gca ggt     546
Asn Lys Glu Asn Val Phe His Gly Thr Lys Asp Thr Ser Gly Ala Gly
            140                 145                 150 gca ggg cga ggg gcc gat ccc cgg gtc cct ccg tcg tcg ccc gcc act     594
Ala Gly Arg Gly Ala Asp Pro Arg Val Pro Pro Ser Ser Pro Ala Thr
        155                 160                 165 cag gtg tgc ttt gag gaa cca cag cca tca aca tcg acg tca gac ctc     642
Gln Val Cys Phe Glu Glu Pro Gln Pro Ser Thr Ser Thr Ser Asp Leu
    170                 175                 180 ttc ccc aca gcc tcg gcc tct tcc acg gag cct tct cct gca ggg cga     690
Phe Pro Thr Ala Ser Ala Ser Ser Thr Glu Pro Ser Pro Ala Gly Arg
185                 190                 195                 200
```

-continued

| | |
|---|---|
| gag cgt tcc tcc agt tgt ggg tct ggg ggt ggt ggc atc tcc cct aaa<br>Glu Arg Ser Ser Ser Cys Gly Ser Gly Gly Gly Gly Ile Ser Pro Lys<br>205                               210                      215 | 738 |
| gga agt ggt ccc tct gtg gca agt gat gaa gtc tcc agc ttt gcc tca<br>Gly Ser Gly Pro Ser Val Ala Ser Asp Glu Val Ser Ser Phe Ala Ser<br>                220                      225                      230 | 786 |
| gct ctc cca gac aga aag act gcg tcc ttt tcg tcg ttg gaa ccc cag<br>Ala Leu Pro Asp Arg Lys Thr Ala Ser Phe Ser Ser Leu Glu Pro Gln<br>                235                      240                      245 | 834 |
| gat cag gag gat ttg gag ccc gtg aag aag aaa atg aga gga gat ggg<br>Asp Gln Glu Asp Leu Glu Pro Val Lys Lys Lys Met Arg Gly Asp Gly<br>250                               255                      260 | 882 |
| gac ctt gac ctg aac ggg cag ttg ttg gtc gca caa ccg cgt aga aat<br>Asp Leu Asp Leu Asn Gly Gln Leu Leu Val Ala Gln Pro Arg Arg Asn<br>265                               270                      275                      280 | 930 |
| gcc caa acc gtc cac gag gac gtc aga gca gcg gct ggg aag cca gac<br>Ala Gln Thr Val His Glu Asp Val Arg Ala Ala Ala Gly Lys Pro Asp<br>                285                      290                      295 | 978 |
| aag atg gag gag acg ctg aca tgc atc atc tgc cag gac ctg ctg cac<br>Lys Met Glu Glu Thr Leu Thr Cys Ile Ile Cys Gln Asp Leu Leu His<br>                  300                      305                      310 | 1026 |
| gac tgc gtg agt ttg cag ccc tgc atg cac acg ttc tgc gcg gct tgc<br>Asp Cys Val Ser Leu Gln Pro Cys Met His Thr Phe Cys Ala Ala Cys<br>                315                      320                      325 | 1074 |
| tac tcg ggc tgg atg gag cgc tcg tcc ctg tgt cct acc tgc cgc tgt<br>Tyr Ser Gly Trp Met Glu Arg Ser Ser Leu Cys Pro Thr Cys Arg Cys<br>330                               335                      340 | 1122 |
| ccc gtg gag cgg atc tgt aaa aac cac atc ctc aac aac ctc gtg gaa<br>Pro Val Glu Arg Ile Cys Lys Asn His Ile Leu Asn Asn Leu Val Glu<br>345                               350                      355                      360 | 1170 |
| gca tac ctc atc cag cat cca gac aag agt cgc agt gaa gaa gat gtg<br>Ala Tyr Leu Ile Gln His Pro Asp Lys Ser Arg Ser Glu Glu Asp Val<br>                365                      370                      375 | 1218 |
| caa agt atg gat gcc agg aat aaa atc act caa gac atg ctg cag ccc<br>Gln Ser Met Asp Ala Arg Asn Lys Ile Thr Gln Asp Met Leu Gln Pro<br>                  380                      385                      390 | 1266 |
| aaa gtc agg cgg tct ttt tct gat gaa gaa ggg agt tca gag gac ctg<br>Lys Val Arg Arg Ser Phe Ser Asp Glu Glu Gly Ser Ser Glu Asp Leu<br>                395                      400                      405 | 1314 |
| ctg gag ctg tca gac gtt gac agt gag tcc tca gac att agc cag cca<br>Leu Glu Leu Ser Asp Val Asp Ser Glu Ser Ser Asp Ile Ser Gln Pro<br>410                               415                      420 | 1362 |
| tac gtc gtg tgc cgg cag tgt cct gag tac aga agg cag gcg gcg cag<br>Tyr Val Val Cys Arg Gln Cys Pro Glu Tyr Arg Arg Gln Ala Ala Gln<br>425                               430                      435                      440 | 1410 |
| cct ccc cac tgc cca gca ccc gag ggc gag cca gga gcc cca cag gcc<br>Pro Pro His Cys Pro Ala Pro Glu Gly Glu Pro Gly Ala Pro Gln Ala<br>                445                      450                      455 | 1458 |
| ctg ggg gat gca ccc tcc acg tcc gtc agc ctg acg aca gca gtc cag<br>Leu Gly Asp Ala Pro Ser Thr Ser Val Ser Leu Thr Thr Ala Val Gln<br>                460                      465                      470 | 1506 |
| gat tac gtg tgc cct ctg caa gga agc cac gcc ctg tgc acc tgc tgc<br>Asp Tyr Val Cys Pro Leu Gln Gly Ser His Ala Leu Cys Thr Cys Cys<br>                475                      480                      485 | 1554 |
| ttc cag ccc atg ccc gac cgg aga gcg gag cgc gag cag gac ccg cgt<br>Phe Gln Pro Met Pro Asp Arg Arg Ala Glu Arg Glu Gln Asp Pro Arg<br>                490                      495                      500 | 1602 |
| gtc gcc cct cag cag tgt gcg gtc tgc ctg cag cct ttc tgc cac ctg<br>Val Ala Pro Gln Gln Cys Ala Val Cys Leu Gln Pro Phe Cys His Leu<br>505                               510                      515                      520 | 1650 |

-continued

```
tac tgg ggc tgc acc cgg acc ggc tgc tac ggc tgc ctg gcc ccg ttt      1698
Tyr Trp Gly Cys Thr Arg Thr Gly Cys Tyr Gly Cys Leu Ala Pro Phe
            525                 530                 535 tgt gag ctc aac ctg ggt gac aag tgt ctg gac ggc gtg ctg aac aac      1746
Cys Glu Leu Asn Leu Gly Asp Lys Cys Leu Asp Gly Val Leu Asn Asn
        540                 545                 550 aac agc tac gag tca gac atc ctg aag aat tac ctg gca acc aga ggt      1794
Asn Ser Tyr Glu Ser Asp Ile Leu Lys Asn Tyr Leu Ala Thr Arg Gly
    555                 560                 565 ttg aca tgg aaa aac atg ttg acc gag agc ctc gtg gct ctc cag cgg      1842
Leu Thr Trp Lys Asn Met Leu Thr Glu Ser Leu Val Ala Leu Gln Arg
570                 575                 580 gga gtg ttt ctg ctg tct gat tac aga gtc acg gga gac acc gtt ctg      1890
Gly Val Phe Leu Leu Ser Asp Tyr Arg Val Thr Gly Asp Thr Val Leu
585                 590                 595                 600 tgt tac tgc tgt ggc ctg cgc agc ttc cgt gag ctg acc tat cag tat      1938
Cys Tyr Cys Cys Gly Leu Arg Ser Phe Arg Glu Leu Thr Tyr Gln Tyr
                605                 610                 615 cgg cag aac att cct gct tcc gag ttg cca gtg gcc gta aca tcc cgt      1986
Arg Gln Asn Ile Pro Ala Ser Glu Leu Pro Val Ala Val Thr Ser Arg
            620                 625                 630 cct gac tgc tac tgg ggc cgt aac tgc cgc act cag gtg aaa gct cac      2034
Pro Asp Cys Tyr Trp Gly Arg Asn Cys Arg Thr Gln Val Lys Ala His
        635                 640                 645 cac gcc atg aaa ttc aat cat atc tgt gaa cag aca agg ttc aaa aac      2082
His Ala Met Lys Phe Asn His Ile Cys Glu Gln Thr Arg Phe Lys Asn
    650                 655                 660 taagcatcca gaggccctga gcagctttca gcactggagg tgaagagagc gtgttttaa     2142 aatacagaga caagcacgtc aaggtgtttt cacagccccc tgagggaagg gacgcagggt    2202
ctccgacagg tgctctgggg tgactcttct gtggagcttt ttaccctctg agtgagaccc    2262
tccccagagc cccgggggcc gcagcccgcc tcctggtga gcgctgggca gggctcgtgg     2322
tggcatcagc agcagagacg aagccttct gtaacatgcg gccgtcccgc cgagaggggc    2382
agttttgctc ttttgtacat tttccgaaac tacagttaaa gcagaagtct gttttcagga    2442
aaagtttcaa gggagaaggg caagtttatc aaaaacattg tttcaggaga agggagcata    2502
agtttacagc ctacaggacg tacacaatat cctgctgctg ggaaaaccac agcatttat    2562 ctatttttta ttttaatagg tttggtgctt atcttctaat aagatttaaa tgtcacaaac    2622
tgtagcacaa ataatataat ttataattta caaattgaca aaaaaaaaa aaaaaaa       2679
```

<210> SEQ ID NO 2
<211> LENGTH: 664
<212> TYPE: PRT
<213> ORGANISM: Homo sapiens

<400> SEQUENCE: 2

```
Met Glu Arg Pro Glu Gly Lys Gln Ser Pro Pro Gln Pro Trp
  1               5                  10                  15

Gly Arg Leu Leu Arg Leu Gly Ala Glu Glu Gly Glu Pro His Val Leu
                20                  25                  30

Leu Arg Lys Arg Glu Trp Thr Ile Gly Arg Arg Gly Cys Asp Leu
             35                  40                  45

Ser Phe Pro Ser Asn Lys Leu Val Ser Gly Asp His Cys Arg Ile Val
         50                  55                  60

Val Asp Glu Lys Ser Gly Gln Val Thr Leu Glu Asp Thr Ser Thr Ser
 65                  70                  75                  80
```

-continued

```
Gly Thr Val Ile Asn Lys Leu Lys Val Lys Lys Gln Thr Cys Pro
                 85                  90                  95

Leu Gln Thr Gly Asp Val Ile Tyr Leu Val Tyr Arg Lys Asn Glu Pro
                100                 105                 110

Glu His Asn Val Ala Tyr Leu Tyr Glu Ser Leu Ser Glu Lys Gln Gly
            115                 120                 125

Met Thr Gln Glu Ser Phe Glu Ala Asn Lys Glu Asn Val Phe His Gly
    130                 135                 140

Thr Lys Asp Thr Ser Gly Ala Gly Ala Gly Arg Gly Ala Asp Pro Arg
145                 150                 155                 160

Val Pro Pro Ser Ser Pro Ala Thr Gln Val Cys Phe Glu Glu Pro Gln
                165                 170                 175

Pro Ser Thr Ser Thr Ser Asp Leu Phe Pro Thr Ala Ser Ala Ser Ser
            180                 185                 190

Thr Glu Pro Ser Pro Ala Gly Arg Glu Arg Ser Ser Ser Cys Gly Ser
        195                 200                 205

Gly Gly Gly Gly Ile Ser Pro Lys Gly Ser Gly Pro Ser Val Ala Ser
210                 215                 220

Asp Glu Val Ser Ser Phe Ala Ser Ala Leu Pro Asp Arg Lys Thr Ala
225                 230                 235                 240

Ser Phe Ser Ser Leu Glu Pro Gln Asp Gln Glu Asp Leu Glu Pro Val
                245                 250                 255

Lys Lys Lys Met Arg Gly Asp Gly Asp Leu Asp Leu Asn Gly Gln Leu
            260                 265                 270

Leu Val Ala Gln Pro Arg Arg Asn Ala Gln Thr Val His Glu Asp Val
        275                 280                 285

Arg Ala Ala Gly Lys Pro Asp Lys Met Glu Glu Thr Leu Thr Cys
290                 295                 300

Ile Ile Cys Gln Asp Leu Leu His Asp Cys Val Ser Leu Gln Pro Cys
305                 310                 315                 320

Met His Thr Phe Cys Ala Ala Cys Tyr Ser Gly Trp Met Glu Arg Ser
                325                 330                 335

Ser Leu Cys Pro Thr Cys Arg Cys Pro Val Glu Arg Ile Cys Lys Asn
            340                 345                 350

His Ile Leu Asn Asn Leu Val Glu Ala Tyr Leu Ile Gln His Pro Asp
        355                 360                 365

Lys Ser Arg Ser Glu Glu Asp Val Gln Ser Met Asp Ala Arg Asn Lys
370                 375                 380

Ile Thr Gln Asp Met Leu Gln Pro Lys Val Arg Arg Ser Phe Ser Asp
385                 390                 395                 400

Glu Glu Gly Ser Ser Glu Asp Leu Leu Glu Leu Ser Asp Val Asp Ser
                405                 410                 415

Glu Ser Ser Asp Ile Ser Gln Pro Tyr Val Val Cys Arg Gln Cys Pro
            420                 425                 430

Glu Tyr Arg Arg Gln Ala Ala Gln Pro Pro His Cys Pro Ala Pro Glu
        435                 440                 445

Gly Glu Pro Gly Ala Pro Gln Ala Leu Gly Asp Ala Pro Ser Thr Ser
    450                 455                 460

Val Ser Leu Thr Thr Ala Val Gln Asp Tyr Val Cys Pro Leu Gln Gly
465                 470                 475                 480

Ser His Ala Leu Cys Thr Cys Cys Phe Gln Pro Met Pro Asp Arg Arg
                485                 490                 495
```

-continued

```
Ala Glu Arg Glu Gln Asp Pro Arg Val Ala Pro Gln Cys Ala Val
        500                 505                 510

Cys Leu Gln Pro Phe Cys His Leu Tyr Trp Gly Cys Thr Arg Thr Gly
        515                 520                 525

Cys Tyr Gly Cys Leu Ala Pro Phe Cys Glu Leu Asn Leu Gly Asp Lys
        530                 535                 540

Cys Leu Asp Gly Val Leu Asn Asn Ser Tyr Glu Ser Asp Ile Leu
545                 550                 555                 560

Lys Asn Tyr Leu Ala Thr Arg Gly Leu Thr Trp Lys Asn Met Leu Thr
                565                 570                 575

Glu Ser Leu Val Ala Leu Gln Arg Gly Val Phe Leu Leu Ser Asp Tyr
                580                 585                 590

Arg Val Thr Gly Asp Thr Val Leu Cys Tyr Cys Cys Gly Leu Arg Ser
            595                 600                 605

Phe Arg Glu Leu Thr Tyr Gln Tyr Arg Gln Asn Ile Pro Ala Ser Glu
        610                 615                 620

Leu Pro Val Ala Val Thr Ser Arg Pro Asp Cys Tyr Trp Gly Arg Asn
625                 630                 635                 640

Cys Arg Thr Gln Val Lys Ala His His Ala Met Lys Phe Asn His Ile
                645                 650                 655

Cys Glu Gln Thr Arg Phe Lys Asn
            660
```

<210> SEQ ID NO 3
<211> LENGTH: 76
<212> TYPE: PRT
<213> ORGANISM: Rad53_sc

<400> SEQUENCE: 3

```
Val Leu Lys Glu Lys Arg Ser Ile Lys Lys Val Trp Thr Phe Gly Arg
  1               5                  10                  15

Asn Pro Ala Cys Asp Tyr His Leu Gly Asn Ile Ser Arg Leu Ser Asn
            20                  25                  30

Lys His Phe Gln Ile Leu Leu Gly Glu Asp Gly Asn Leu Leu Leu Asn
        35                  40                  45

Asp Ile Ser Thr Asn Gly Thr Trp Leu Asn Gly Gln Lys Val Glu Arg
    50                  55                  60

Asn Ser Asn Gln Leu Leu Ser Gln Gly Asp Glu Ile
65                  70                  75
```

<210> SEQ ID NO 4
<211> LENGTH: 85
<212> TYPE: PRT
<213> ORGANISM: Dma1_ap

<400> SEQUENCE: 4

```
Tyr Trp Asn Arg Lys Gln Asn Asn Leu Pro Ile Tyr Ile Gly Arg Tyr
  1               5                  10                  15

Thr Glu Arg Tyr Asn Gly Gly Asp Val Ser Ala Ile Val Phe Arg Ser
            20                  25                  30

Lys Val Val Ser Arg Arg His Ala Gln Ile Phe Tyr Glu Asn Asn Thr
        35                  40                  45

Trp Tyr Ile Gln Asp Met Gly Ser Ser Gly Thr Phe Leu Asn His
    50                  55                  60

Val Arg Leu Ser Pro Pro Ser Lys Thr Ser Lys Pro Tyr Pro Ile Ser
65                  70                  75                  80
```

-continued

```
Asn Asn Asp Ile Leu
                85

<210> SEQ ID NO 5
<211> LENGTH: 93
<212> TYPE: PRT
<213> ORGANISM: YNL116w_sc

<400> SEQUENCE: 5

Pro Ile Ile Arg Lys Ala Gly Pro Gly Ser Gln Leu Val Ile Gly Arg
  1               5                  10                  15

Tyr Thr Glu Arg Val Arg Asp Ala Ile Ser Lys Ile Pro Glu Gln Tyr
             20                  25                  30

His Pro Val Val Phe Lys Ser Lys Val Val Ser Arg Thr His Gly Cys
         35                  40                  45

Phe Lys Val Asp Ser Gln Gly Asn Trp Tyr Ile Lys Asp Val Lys Ser
     50                  55                  60

Ser Ser Gly Thr Phe Leu Asn His Gln Arg Leu Ser Pro Ala Ser Ser
 65                  70                  75                  80

Leu Ser Lys Asp Thr Pro Leu Arg Asp Gly Asp Ile Leu
                 85                  90

<210> SEQ ID NO 6
<211> LENGTH: 44
<212> TYPE: PRT
<213> ORGANISM: ICP0_vzv

<400> SEQUENCE: 6

Thr Cys Thr Ile Cys Met Ser Thr Val Ser Asp Leu Gly Lys Thr Met
  1               5                  10                  15

Pro Cys Asp His Asp Phe Cys Phe Val Cys Ile Arg Ala Trp Thr Ser
             20                  25                  30

Thr Ser Val Gln Cys Pro Leu Cys Arg Cys Pro Val
         35                  40

<210> SEQ ID NO 7
<211> LENGTH: 49
<212> TYPE: PRT
<213> ORGANISM: Dma1_ap

<400> SEQUENCE: 7

Glu Cys Cys Ile Cys Leu Met Pro Val Leu Pro Cys Gln Ala Leu Phe
  1               5                  10                  15

Val Ala Pro Cys Ser His Ser Tyr His Tyr Lys Cys Ile Arg Pro Thr
             20                  25                  30

Leu Asn Glu Ser His Pro Tyr Phe Ser Cys Phe Ile Cys Arg Lys Tyr
         35                  40                  45

His

<210> SEQ ID NO 8
<211> LENGTH: 49
<212> TYPE: PRT
<213> ORGANISM: YNL116w_sc

<400> SEQUENCE: 8

Asp Cys Ser Ile Cys Leu Cys Lys Ile Lys Pro Cys Gln Ala Ile Phe
  1               5                  10                  15

Ile Ser Pro Cys Ala His Ser Trp His Phe Arg Cys Val Arg Arg Leu
             20                  25                  30
```

-continued

```
Val Met Leu Ser Tyr Pro Gln Phe Val Cys Pro Asn Cys Arg Ser Ser
 35                  40                  45
Cys

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
tgtctcttga cagcggc                                                  17

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
catggaacac attttccttg                                               20

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
aaagaattct ggaagatacc agcaccag                                      28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
aaaaagcttg gcagatgatg catgtcag                                      28

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
aaagaattcc tcccctaaag gaagtg                                        26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:
      oligonucleotide
```

-continued

```
<400> SEQUENCE: 14
aaaaagcttt caacgtctga cagctc                                              26

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
aagaaaatga gaggagatgg                                                     20

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
ggttgagctc acaaaacg                                                       18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
aagaaaatga gaggagatgg                                                     20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
tccagacact tgtcacc                                                        17

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
aagaaaatga gaggagatgg                                                     20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
```
agacagcaga aacactcc                                          18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
accacatcct caacaacc                                          18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
ggttgagctc acaaaacg                                          18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
accacatcct caacaacc                                          18

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 24
tccagacact tgtcacc                                           17

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
atacctcatc cagcatcc                                          18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 26

```
ggttgagctc acaaaacg                                               18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27
atacctcatc cagcatcc                                               18

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 28
tccagacact tgtcacc                                                17

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 29
atacctcatc cagcatcc                                               18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 30
agacagcaga aacactcc                                               18

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 31
aaagaattcc agcctttctg ccacc                                       25

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 32
aaaaagcttt ccacagaaga gtcaccc                                              27
```